(12) United States Patent
Lee et al.

(10) Patent No.: US 11,865,345 B2
(45) Date of Patent: *Jan. 9, 2024

(54) DISPLAY OF REGION OF ACTIVATION IN NEUROSTIMULATION PROGRAMMING SCREEN

(71) Applicant: Boston Scientific Neuromodulation Corporation, Valencia, CA (US)

(72) Inventors: Dongchul Lee, Agua Dulce, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/739,931

(22) Filed: May 9, 2022

(65) Prior Publication Data

US 2022/0257951 A1    Aug. 18, 2022

Related U.S. Application Data

(63) Continuation of application No. 16/246,758, filed on Jan. 14, 2019, now Pat. No. 11,344,730, which is a
(Continued)

(51) Int. Cl.
*A61N 1/36* (2006.01)
*A61N 1/372* (2006.01)

(52) U.S. Cl.
CPC ..... *A61N 1/36146* (2013.01); *A61N 1/37247* (2013.01)

(58) Field of Classification Search
CPC ................................. A61N 1/36146
See application file for complete search history.

(56) References Cited

U.S. PATENT DOCUMENTS 6,516,227 B1    2/2003   Meadows et al.
6,895,280 B2    5/2005   Meadows et al.
(Continued)

FOREIGN PATENT DOCUMENTS

EP    2709721 A1    3/2014
EP    2709721 B1    9/2016
(Continued)

OTHER PUBLICATIONS

"U.S. Appl. No. 13/506,832, Non Final Office Action dated Apr. 24, 2015", 12 pgs.
(Continued)

*Primary Examiner* — Catherine M Voorhees
*Assistant Examiner* — Roland Dinga
(74) *Attorney, Agent, or Firm* — Schwegman Lundberg & Woessner, P.A.

(57) ABSTRACT

A system for use with a neurostimulator coupled to one or more electrodes implanted adjacent neural tissue of a patient. The system comprises a user input device configured for allowing a user to select different nerve fiber diameters and to select a set of stimulation parameters. The system further comprises processing circuitry configured estimating regions of activation within the neural tissue of the patient based on the selected nerve fiber diameters and the selected stimulation parameter set. The system further comprises a display device configured for displaying the estimated regions of tissue activation. The user input device may further be configured for allowing the user to select different tissue regions of therapy, in which case, the display device may display the different tissue region on a human body map, and different indicia associating the displayed tissue regions for therapy to displayed estimated regions of tissue activation.

20 Claims, 18 Drawing Sheets

Related U.S. Application Data continuation of application No. 15/707,209, filed on Sep. 18, 2017, now Pat. No. 10,195,440, which is a continuation of application No. 13/506,832, filed on May 17, 2012, now Pat. No. 9,764,140.

(60) Provisional application No. 61/486,922, filed on May 17, 2011.

(56) References Cited

U.S. PATENT DOCUMENTS

| | | | |
|---|---|---|---|
| 6,993,384 | B2 | 1/2006 | Bradley et al. |
| 7,623,918 | B2 | 11/2009 | Goetz |
| 9,764,140 | B2 | 9/2017 | Lee et al. |
| 10,195,440 | B2 | 2/2019 | Lee et al. |
| 11,344,730 | B2* | 5/2022 | Lee .................... A61N 1/36146 |
| 2006/0017749 | A1 | 1/2006 | McIntyre et al. |
| 2007/0203541 | A1 | 8/2007 | Goetz et al. |
| 2007/0288064 | A1 | 12/2007 | Butson et al. |
| 2009/0281595 | A1 | 11/2009 | King et al. |
| 2009/0281596 | A1 | 11/2009 | King et al. |
| 2010/0010566 | A1* | 1/2010 | Thacker ............. A61N 1/36167 607/46 |
| 2010/0121409 | A1* | 5/2010 | Kothandaraman ......................... A61N 1/36157 607/46 |
| 2010/0137944 | A1 | 6/2010 | Zhu |
| 2010/0241195 | A1 | 9/2010 | Meadows et al. |
| 2011/0106215 | A1 | 5/2011 | Moffitt |
| 2012/0046715 | A1 | 2/2012 | Moffitt et al. |
| 2012/0109257 | A1 | 5/2012 | Yoo et al. |
| 2012/0165900 | A1 | 6/2012 | Zhu et al. |
| 2012/0265271 | A1 | 10/2012 | Goetz |
| 2012/0296392 | A1 | 11/2012 | Lee et al. |
| 2018/0001092 | A1 | 1/2018 | Lee et al. |
| 2019/0143121 | A1 | 5/2019 | Lee et al. |

FOREIGN PATENT DOCUMENTS

| | | |
|---|---|---|
| JP | 6073866 | 1/2017 |
| WO | WO-2011025865 A1 | 3/2011 |

OTHER PUBLICATIONS

"U.S. Appl. No. 13/506,832, Non Final Office Action dated May 2016", 11 pgs.
"U.S. Appl. No. 13/506,832, Non Final Office Action dated Nov. 6, 2015", 13 pgs.
"U.S. Appl. No. 13/506,832, Non Final Office Action dated Dec. 20, 2016", 12 pgs.
"U.S. Appl. No. 13/506,832, Notice of Allowance dated May 12, 2017", 8 pgs.
"U.S. Appl. No. 13/506,832, Response filed Feb. 1, 2016 to Non Final Office Action dated Nov. 6, 2015", 11 pgs.
"U.S. Appl. No. 13/506,832, Response filed Mar. 14, 2017 to Non Final Office Action dated Dec. 20, 2016", 10 pgs.
"U.S. Appl. No. 13/506,832, Response filed Jul. 24, 2015 to Non Final Office Action dated Apr. 24, 2015", 11 pgs.
"U.S. Appl. No. 13/506,832, Response filed Aug. 22, 2016 to Non Final Office Action dated May 20, 2016", 13 pgs.
"U.S. Appl. No. 15/707,209, Final Office Action dated Jun. 26, 2018", 6 pgs.
"U.S. Appl. No. 15/707,209, Non Final Office Action dated Dec. 1, 2017", 10 pgs.
"U.S. Appl. No. 15/707,209, Notice of Allowance dated Sep. 26, 2018", 8 pgs.
"U.S. Appl. No. 15/707,209, Preliminary Amendment filed Sep. 19, 2017", 7 pgs.
"U.S. Appl. No. 15/707,209, Response filed Mar. 1, 2018 to Non Final Office Action dated Dec. 1, 2017", 9 pgs.
"U.S. Appl. No. 15/707,209, Response filed Aug. 27, 2018 to Final Office Action dated Jun. 26, 2018", 8 pgs.
"U.S. Appl. No. 16/246,758, Advisory Action dated Feb. 24, 2021", 2 pgs.
"U.S. Appl. No. 16/246,758, Examiner Interview Summary dated Aug. 11, 2021", 2 pgs.
"U.S. Appl. No. 16/246,758, Final Office Action dated Nov. 24, 2021", 9 pgs.
"U.S. Appl. No. 16/246,758, Final Office Action dated Nov. 30, 2020", 10 pgs.
"U.S. Appl. No. 16/246,758, Non Final Office Action dated May 7, 2021", 8 pgs.
"U.S. Appl. No. 16/246,758, Non Final Office Action dated Jun. 1, 2020", 7 pgs.
"U.S. Appl. No. 16/246,758, Notice of Allowance dated Jan. 28, 2022", 10 pgs.
"U.S. Appl. No. 16/246,758, Preliminary Amendment filed Feb. 13, 2019", 6 pgs.
"U.S. Appl. No. 16/246,758, Response filed Feb. 15, 2021 to Final Office Action dated Nov. 30, 2020", 9 pgs.
"U.S. Appl. No. 16/246,758, Response filed Aug. 9, 2021 to Non Final Office Action dated May 7, 2021", 9 pgs.
"U.S. Appl. No. 16/246,758, Response filed Aug. 24, 2020 to Non Final Office Action dated Jun. 1, 2020", 6 pgs.
"U.S. Appl. No. 16/246,758, Response filed Dec. 27, 2021 to Final Office Action dated Nov. 24, 2021", 9 pgs.
"Australian Application Serial No. 2012255708, First Examiner Report dated Nov. 30, 2015", 3 pgs.
"Australian Application Serial No. 2012255708, Response filed Oct. 28, 2016 to Subsequent Examiners Report dated Sep. 19, 2016", 23 pgs.
"Australian Application Serial No. 2012255708, Subsequent Examiners Reprt dated Sep. 19, 2016", 3 pgs.
"European Application Serial No. 12724261.8, Examination Notification Art. 94(3) dated Aug. 13, 2015", 5 pgs.
"European Application Serial No. 12724261.8, Office Action dated Dec. 23, 2014", 5 pgs.
"International Application Serial No. PCT/US2012/038288, International Preliminary Report on Patentability dated Nov. 28, 2013", 7 pgs.
"International Application Serial No. PCT/US2012/038288, International Search Report dated Jul. 13, 2012", 3 pgs.
"International Application Serial No. PCT/US2012/038288, Written Opinion dated Jul. 13, 2012", 5 pgs.
"Japanese Application Serial No. 2014-511520, Amendment filed Jan. 5, 2015", English Claims, 4 pages.
"Japanese Application Serial No. 2014-511520, Office Action dated Feb. 1, 2016", (with partial translation), 4 pgs.
Holsheimer, J, et al., "Clinical Evaluation of Paresthesia Steering with a New System for Spinal Cord Stimulation", Neurosurgery, vol. 42, No. 3, (Mar. 1998), 541-549.
Moffitt, Michael A, et al., "User Interface for Segmented Neurostimulation Leads", U.S. Appl. No. 61/374,879, filed Aug. 18, 2010.
Struijk, J J, et al., "Transverse Tripolar Spinal Cord Stimulation Theoretical Performance of a Dual Channel System", Med. & Biol. Eng. & Comput, (1996), 273-279.
Zhu, Changfang, et al., "Neurostimulation System for Implementing Model-Based Estimate of Neurostimulation Effects", U.S. Appl. No. 61/427,059, filed Dec. 23, 2010.
U.S. Appl. No. 13/506,832 U.S. Pat. No. 9,764,140, filed May 17, 2012, Display of Region of Activation in Neurostimulation Programming Screen.
U.S. Appl. No. 15/707,209 U.S. Pat. No. 10195,440, filed Sep. 18, 2017, Display of Region Activation in Neurostimulation Programming Screen.
U.S. Appl. No. 16/246,758, filed Jan. 14, 2019, Display of Region of Activation in Neurostimulation Programming Screen.

* cited by examiner

ACTIVATED NODES
(14 μm FIBERS)

BOUNDARY OF ACTIVATED NODES
(14 μm FIBERS)

BOUNDARY OF ACTIVATED NODES
(14 μm FIBERS)

ACTIVATED FIBRES
(14 μm FIBRES)

ACTIVATED NODES AND
BOUNDARY PLOT

DISPLAY OF REGION OF ACTIVATION IN NEUROSTIMULATION PROGRAMMING SCREEN

RELATED APPLICATION DATA

The present application is a continuation of U.S. application Ser. No. 16/246,758, filed Jan. 14, 2019, which is a continuation of U.S. application Ser. No. 15/707,209, filed Sep. 18, 2017, now issued as U.S. Pat. No. 10,195,440, which is a continuation of U.S. application Ser. No. 13/506,832, filed May 17, 2012, now issued as U.S. Pat. No. 9,764,140, which claims the benefit under 35 U.S.C. § 119 to U.S. provisional patent application Ser. No. 61/486,922, filed May 17, 2011. Each of the foregoing applications is hereby incorporated by reference into the present application in its entirety.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers appropriate stimulation energy to the volume of tissue that is targeted for therapeutic benefit (e.g., treatment of pain), while minimizing the volume of non-target tissue that is stimulated.

For example, in the context of SCS, to produce the feeling of paresthesia without inducing discomfort or involuntary motor movements within the patient, it is often desirable to preferentially stimulate nerve fibers in the dorsal column (DC) nerve fibers, which primarily include sensory nerve fibers, over nerve fibers in the dorsal root (DR) nerve fibers, which include both sensory nerve fibers and motor reflex nerve fibers. In order to stimulate the DC nerve fibers, while guarding against the stimulation of the DR nerve fibers, tripolar SCS systems may activate anodes that flank a single cathode in a medial-lateral electrical field, with the single cathode providing the stimulation energy for the DC fibers, while the flanking anodes guarding against the over-stimulation of the DR fibers, thereby increasing the therapeutic range of SCS for stimulating the desired DC fibers, while reducing the unwanted side effect of stimulating DR fibers (see J. J. Struijk and J. Holsheimer Tripolar Spinal Cord Stimulation: Theoretical Performance of a Dual Channel System, Medical and Biological Engineering and Computing, Vol. 34, No. 4, 1996, pp. 273-279; J. Holsheimer, B. Nuttin, G. King, W. Wesselink, J. Gybels, and P. de Sutter, Clinical Evaluation of Paresthesia Steering with a New System for Spinal Cord Stimulation, Neurosurgery, Vol. 42, No. 3, 1998, pp. 541-549).

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, a patient care professional (e.g., a clinician, field engineer, sales representative, etc.) generally programs the neurostimulator through a computerized programming system. This programming system can be a self-contained hardware/software system, or can be defined predominantly by software running on a standard personal computer (PC), personal data assistant (PDA), or other computerized device. The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated.

Thus, in the application of electrical neurostimulation therapy, the goal is to identify a pertinent paradigm of stimulation that properly stimulates neural tissue. To aid the patient care professional in correlating the paresthesia experienced by the patient during stimulation and the dermatomes corresponding the region or regions of pain experienced by the patient, computer programming systems typically include dermatome maps of the human body onto which regions of pain and regions of paresthesia experienced by the patient can be recorded to allow the patient care professional to determine the effectiveness of the therapy.

The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the region of activation (ROA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the region of activation (ROA) can often be moved back to the effective pain site without having to re-operate on the patient in order to reposition the lead and its electrode array. When adjusting the region of activation (ROA) relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. In the context of SCS, current steering is typically either performed in a rostro-caudal direction (i.e., along the axis of the spinal cord) or a medial-lateral direction (i.e., perpendicular to the axis of the spinal cord).

In one novel current steering method, described in U.S. patent application Ser. No. 12/938,282, entitled "System and Method for Mapping Arbitrary Electric Fields to Pre-existing Lead Electrodes," which is incorporated herein by reference, a stimulation target in the form of an ideal target pole (e.g., an ideal bipole or tripole) is defined and the stimulation parameters, including the fractionalized current values on each of the electrodes, are computationally determined in a manner that emulates these ideal target poles. It can be appreciated that current steering can be implemented by moving the ideal target poles about the leads, such that the appropriate fractionalized current values for the electrodes are computed for each of the various positions of the ideal target pole. As a result, the current steering can be implemented using an arbitrary number and arrangement of electrodes, thereby solving the afore-described problems.

Significantly, it may sometimes be desirable to estimate or predict the stimulation effects of electrical energy applied, or to be applied, to neural tissue adjacent to electrodes based on an estimation of the membrane response (e.g., transmembrane voltage potentials) of one or more neurons induced by the actually applied or potentially applied electrical energy. For example, given a specific set of stimulation parameters, it may be desired to estimate an ROA within the neural tissue of a patient based on an estimation of the neuronal response, which technique is described in U.S. Provisional Patent Application Ser. No. 61/427,059, entitled "Neurostimulation System For Implementing Model-Based Estimate of Neurostimulation Effects," which is expressly incorporated herein by reference. This estimated ROA can then be displayed to the user for analysis to determine whether the tissue to be targeted for stimulation is likely to be therapeutically stimulated. The estimated region or regions of stimulation with the most effective therapy can then be stored for subsequent use. For example, if the stimulation region(s) is estimated and recorded during an OR mapping procedure, the stimulation region(s) can be recalled and displayed during a subsequent fitting procedure, in which case, they can be used as target region(s) to aid in optimum placement of an ideal target pole.

When estimating the neuronal response, and thus a region of stimulation, nerve fibers of fixed and uniform diameters are assumed. However, because the diameter of nerve fibers running through a spinal cord are not uniform (with the larger diameter nerve fibers being more excitable than smaller diameter nerve fibers), and in fact, may, on average, be substantially different from the diameter of the nerve fiber assumed by the algorithm used to estimate the neuronal response, the resulting estimation of the region of stimulation may be inaccurate. At the least, the display of the estimation region of stimulation may provide an incomplete picture of the region or regions of tissue that are stimulated. Furthermore, in the case where multiple ROAs are estimated and displayed, especially for subsequent use during a fitting procedure, it may be difficult to correlate the displayed ROAs with the corresponding pain regions to be treated.

SUMMARY OF THE INVENTION

In accordance with a first aspect of the present inventions, a system for use with a neurostimulator coupled to one or more electrodes implanted adjacent neural tissue of a patient is provided. The system comprises a user input device configured for allowing a user to select at least one nerve fiber diameter and to select a set of stimulation parameters, processing circuitry configured estimating a region of activation within the neural tissue of the patient based on the selected at least one nerve fiber diameter and the selected stimulation parameter set, and a display device configured for displaying the estimated region of tissue activation. In an optional embodiment, the user input device is configured for allowing the user to select a plurality of different nerve fiber diameters, the processing circuitry is configured for estimating regions of tissue activation respectively based on the selected different nerve fiber diameters, and the display device is configured for concurrently displaying the regions of tissue activation with different indicia (e.g., different colors).

In one embodiment, the processing circuitry is configured for estimating the region of tissue activation by determining whether each of a grid of uniformly spaced nodes is activated, and the display device is configured for displaying a representation of the activated nodes. The user input device may be configured for allowing the user to select a resolution of the grid of nodes (e.g., 0.2 mm-2.0 mm), in which case, the processing circuitry may be configured for estimating the region of tissue activation at the selected resolution of the grid of nodes. The activated nodes may be displayed in any one of a variety of manners. For example, the representation of the activated nodes may comprise discrete geometric shapes (e.g., circles) coincident with the activated nodes. As another example, the representation of the activated nodes may comprise a polygon having vertices coincident with the activated nodes. In addition to estimating the activated nodes for the purpose of estimating the region of tissue activation, the processing circuitry may be configured for estimating an activation of one or more nerve fibers based on the selected at least one nerve fiber diameter and the selected stimulation parameter set, in which case, the display device may be configured for displaying a representation of the activated nerve fiber(s).

The neural tissue adjacent to which the electrodes are implanted may be spinal cord tissue. In the case where the spinal cord tissue comprises DC nerve fibers, the processing circuitry may optionally be configured for determining the intensity of activation within the estimated region of activation at points transversely spaced relative to the DC nerve fibers, and the display device may be configured for displaying a plurality of parallel lines intersecting the points. The parallel lines respectively represent the DC nerve fibers and comprise indicia of the activation intensities determined at the corresponding points, e.g., different thicknesses of the lines, which thicknesses may be in proportion to the intensities at the corresponding points. In the case where the spinal cord tissue comprises DR nerve fibers, the processing circuitry may optionally be configured for estimating an activation of the DR nerve fibers based on the selected at least one nerve fiber diameter and the selected stimulation parameter set, and the display device may be further configured for displaying a representation of the estimated activated DR nerve fibers; e.g., parallel lines corresponding to the estimated activated DR nerve fibers or a polygon defining the boundary of the estimated activated dorsal roots.

In an optional embodiment, the selected stimulation parameter set comprises an electrode combination, the user input device is configured for allowing a user to define an ideal target pole relative to the one or more electrodes, and the processing circuitry is further configured for determining the electrode combination based on the defined ideal target pole. In this case, the display device may be further configured for displaying the ideal target pole relative to the estimated region of tissue activation. The system may further comprise output circuitry configured for transmitting the stimulation parameter set to the neurostimulation device. The system may also comprise an external control device comprising the user input device and the processing circuitry.

In accordance with a second aspect of the present inventions, another system for use with a neurostimulator coupled to one or more electrodes implanted adjacent neural tissue of a patient is provided. The system comprises a user input device configured for allowing a user to select a set of stimulation parameters, processing circuitry configured estimating regions of activation within the neural tissue of the patient respectively based on different nerve fiber diameters and the selected stimulation parameter set, and a display device configured for concurrently displaying the regions of tissue activation with different indicia (e.g., different colors).

In one embodiment, the processing circuitry is configured for estimating the region of tissue activation by determining whether each of a grid of uniformly spaced nodes is activated, and the display device is configured for displaying a representation of the activated nodes. In an optional embodiment, the selected stimulation parameter set comprises an electrode combination, the user input device is configured for allowing a user to define an ideal target pole relative to the one or more electrodes, and the processing circuitry is further configured for determining the electrode combination based on the defined ideal target pole. In this case, the display device may be further configured for displaying the ideal target pole relative to the estimated regions of tissue activation. The system may further comprise output circuitry configured for transmitting the stimulation parameter set to the neurostimulation device. The system may also comprise an external control device comprising the user input device and the processing circuitry.

In accordance with a third aspect of the present inventions, still another system for use with a neurostimulator coupled to one or more electrodes implanted adjacent neural tissue of a patient is provided. The system comprises a user input device configured for allowing a user to select a plurality of stimulation parameter sets and a plurality of different tissue regions for therapy, processing circuitry configured estimating a region of activation within the neural tissue of the patient for each of the selected stimulation parameter sets, and a display device configured for displaying the estimated regions of tissue activation, displaying the plurality of different tissue regions on a human body map, and displaying different indicia (e.g., different colors) associating the displayed tissue regions for therapy to the displayed estimated regions of tissue activation.

In one embodiment, the processing circuitry is configured for estimating each of the regions of tissue activation by determining whether each of a grid of uniformly spaced nodes is activated, and the display device is configured for displaying a representation of the activated nodes for each region of tissue activation. The activated nodes may be displayed in any one of a variety of manners. For example, the representation of the activated nodes may comprise discrete geometric shapes (e.g., circles) coincident with the activated nodes. As another example, the representation of the activated nodes may comprise a polygon having vertices coincident with the activated nodes. The system may further comprise output circuitry configured for transmitting the stimulation parameter set to the neurostimulation device. The system may also comprise an external control device comprising the user input device and the processing circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. The patent or application file contains at least one drawing executed in color. Copies of this patent or patent application publication with color drawing(s) will be provided by the Office upon request and payment of the necessary fee. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
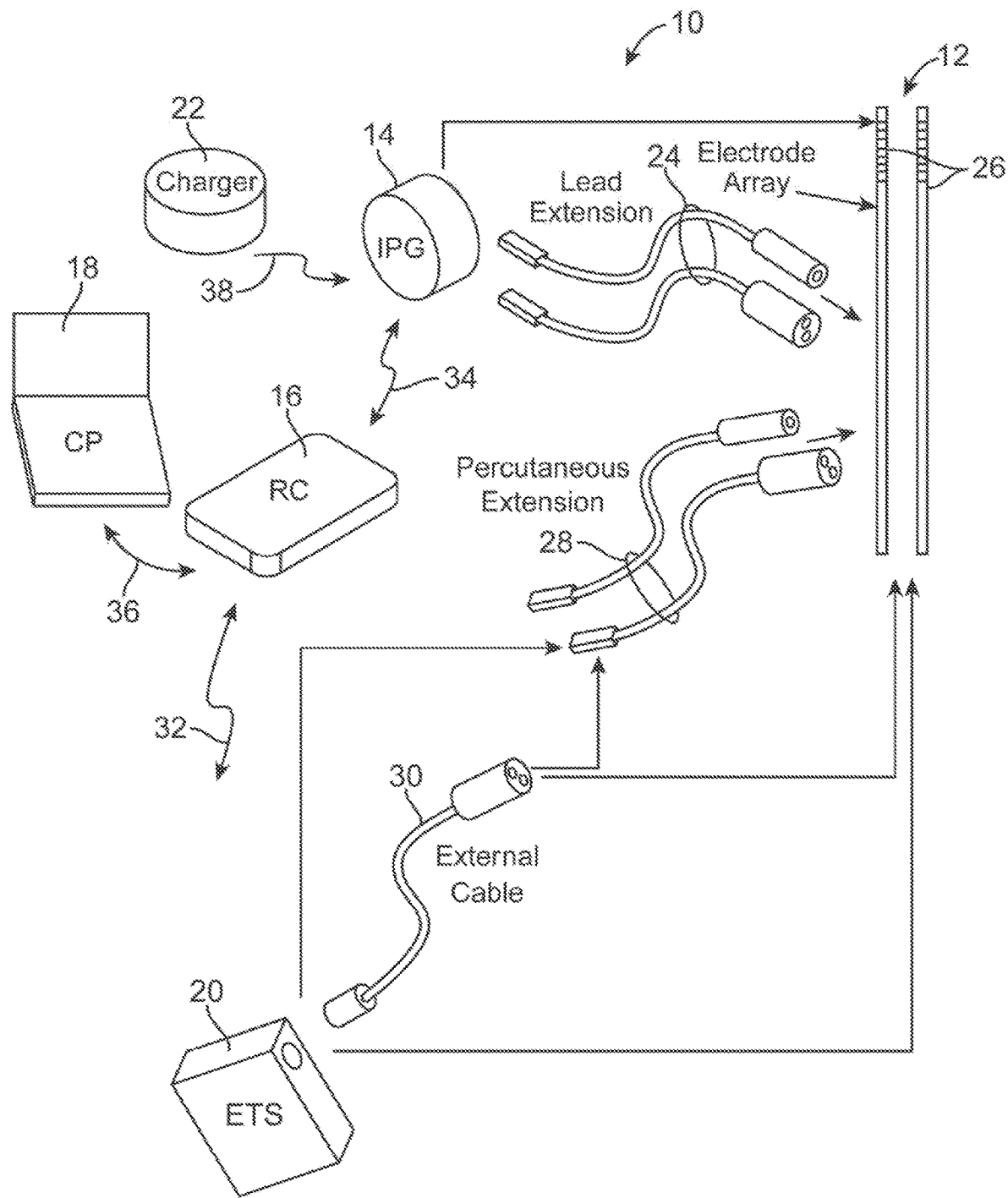
FIG. 1 is a plan view of a Spinal cord Stimulation (SCS) system constructed in accordance with one embodiment of the present inventions.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
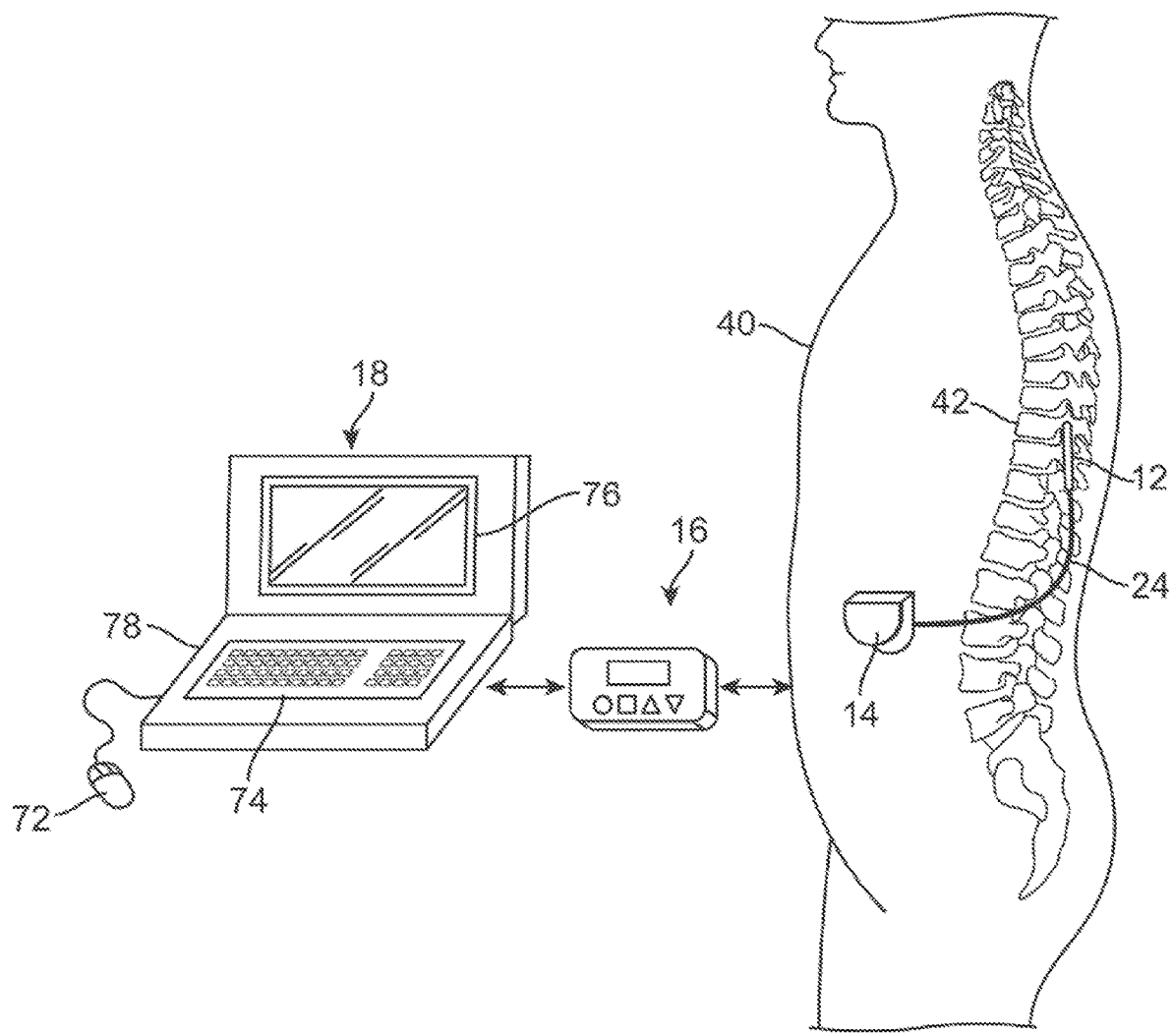
FIG. 2 is a perspective view of the arrangement of the SCS system of FIG. 1 with respect to a patient.

As shown in FIG. 2, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the RC 16.

Figure 3:
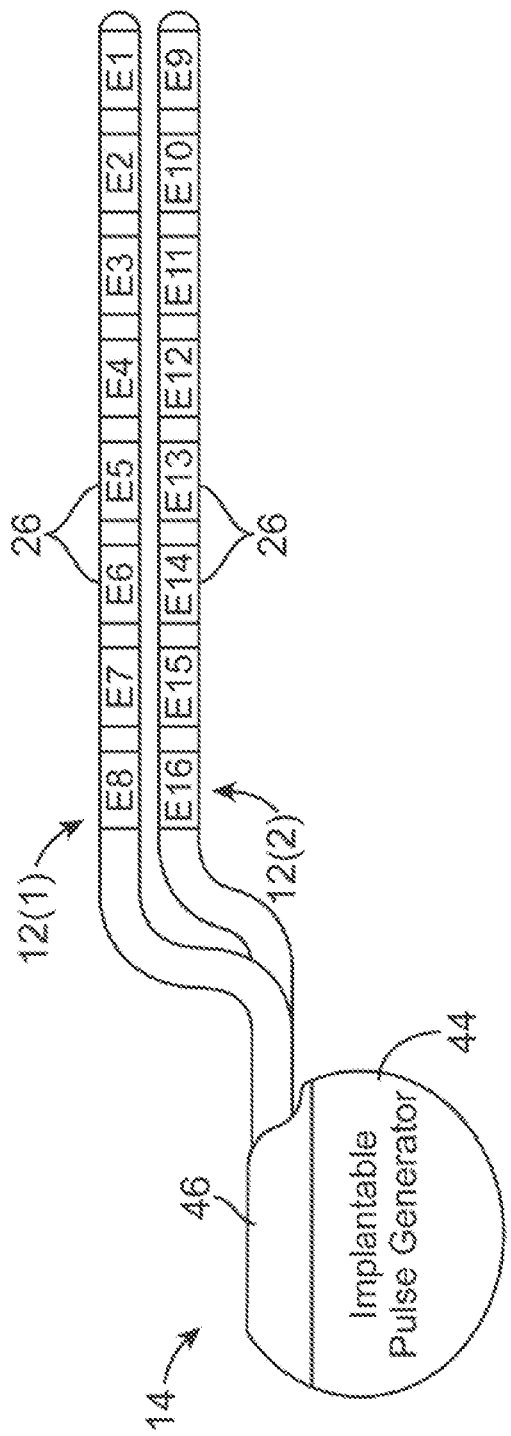
FIG. 3 is a profile view of an implantable pulse generator (IPG) and percutaneous leads used in the SCS system of FIG. 1.

Referring now to FIG. 3, the external features of the neurostimulation leads 12 and the IPG 14 will be briefly described. One of the neurostimulation leads 12(1) has eight electrodes 26 (labeled E1-E8), and the other neurostimulation lead 12(2) has eight electrodes 26 (labeled E9-E16). The actual number and shape of leads and electrodes will, of course, vary according to the intended application. The IPG 14 comprises an outer case 46 for housing the electronic and other components (described in further detail below), and a connector 48 to which the proximal ends of the neurostimulation leads 12 mates in a manner that electrically couples the electrodes 26 to the electronics within the outer case 46. The outer case 46 is composed of an electrically conductive, biocompatible material, such as titanium, and forms a hermetically sealed compartment wherein the internal electronics are protected from the body tissue and fluids. In some cases, the outer case 46 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode combinations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case 46 of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
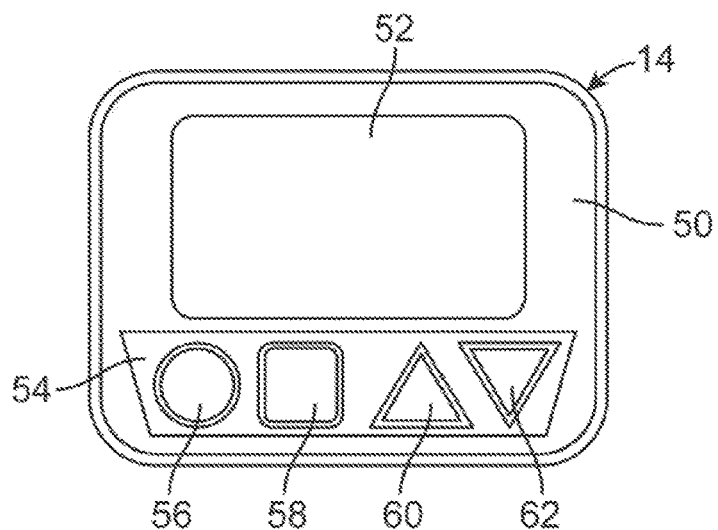
FIG. 4 is front view of a remote control (RC) used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
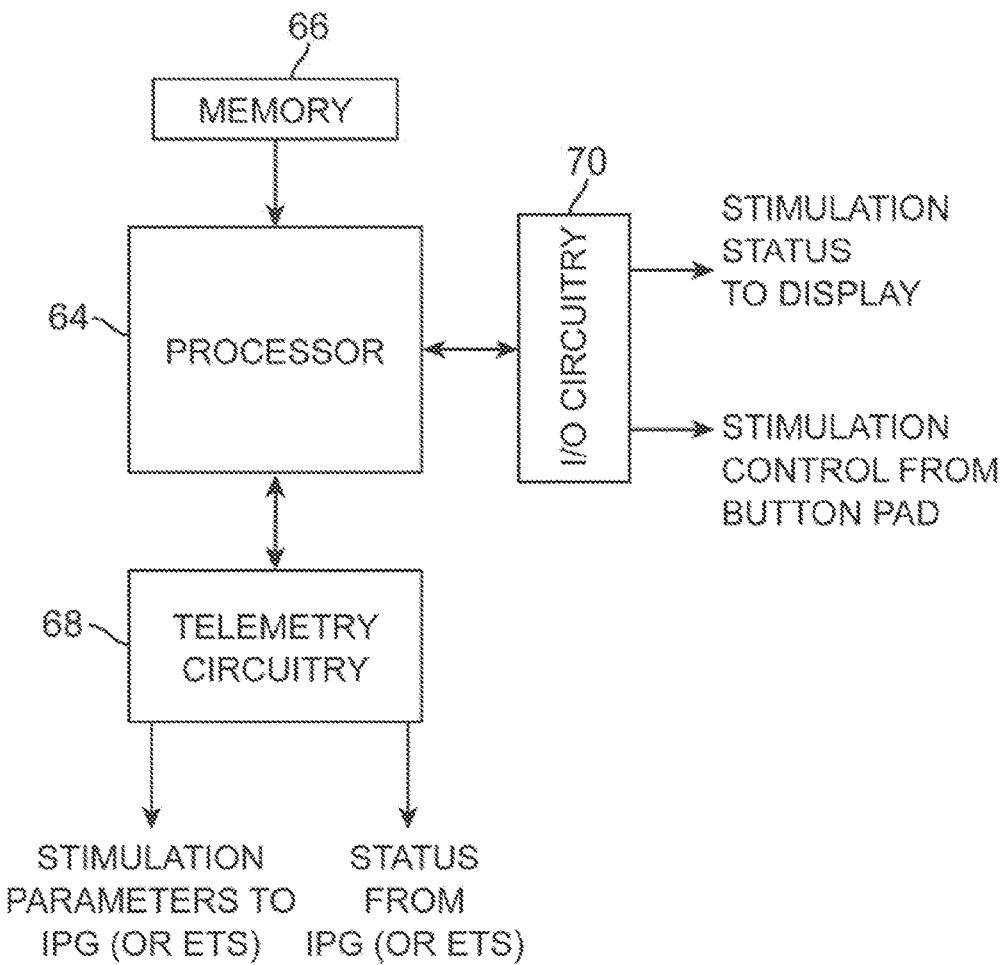
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

Figure 6:
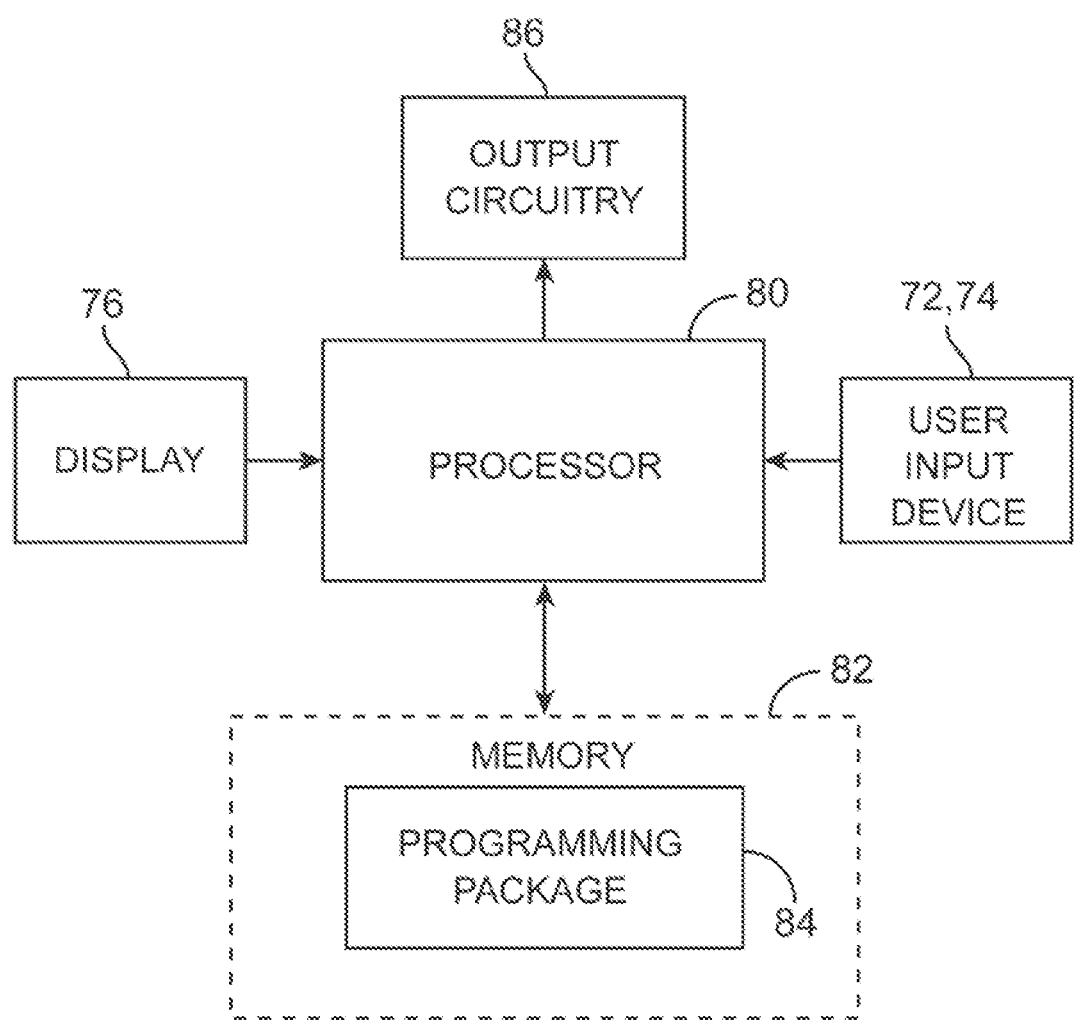
FIG. 6 is a block diagram of the internal components of a clinician's programmer (CP) used in the SCS system of FIG. 1.

Referring further to FIG. 6, to allow the user to perform these functions, the CP 18 includes a mouse 72, a keyboard 74, and a display monitor 76 housed in a housing 78. It is to be understood that in addition to, or in lieu of, the mouse 72, other directional programming devices may be used, such as a joystick, a button pad, a group of keyboard arrow keys, a roller ball tracking device, and horizontal and vertical rocker-type arm switches. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 further includes a processor 80 (e.g., a central processor unit (CPU)) and memory 82 that stores a stimulation programming package 84, which can be executed by the processor 80 to allow the user to program the IPG 14 and RC 16. The CP 18 further includes output circuitry 86 for downloading stimulation parameters to the IPG 14 and RC 16 and for uploading stimulation parameters already stored in the memory 66 of the RC 16, via the telemetry circuitry 68 of the RC 16.

Execution of the programming package 84 by the processor 80 provides a multitude of display screens (not shown) that can be navigated through via use of the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a therapeutic map (e.g., body regions targeted for therapy, body regions for minimization of side effects, along with metrics of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides an efficient means for programming the IPG 14 with stimulation parameters using an estimated region or regions of tissue activation displayed to the user.

Figure 7:
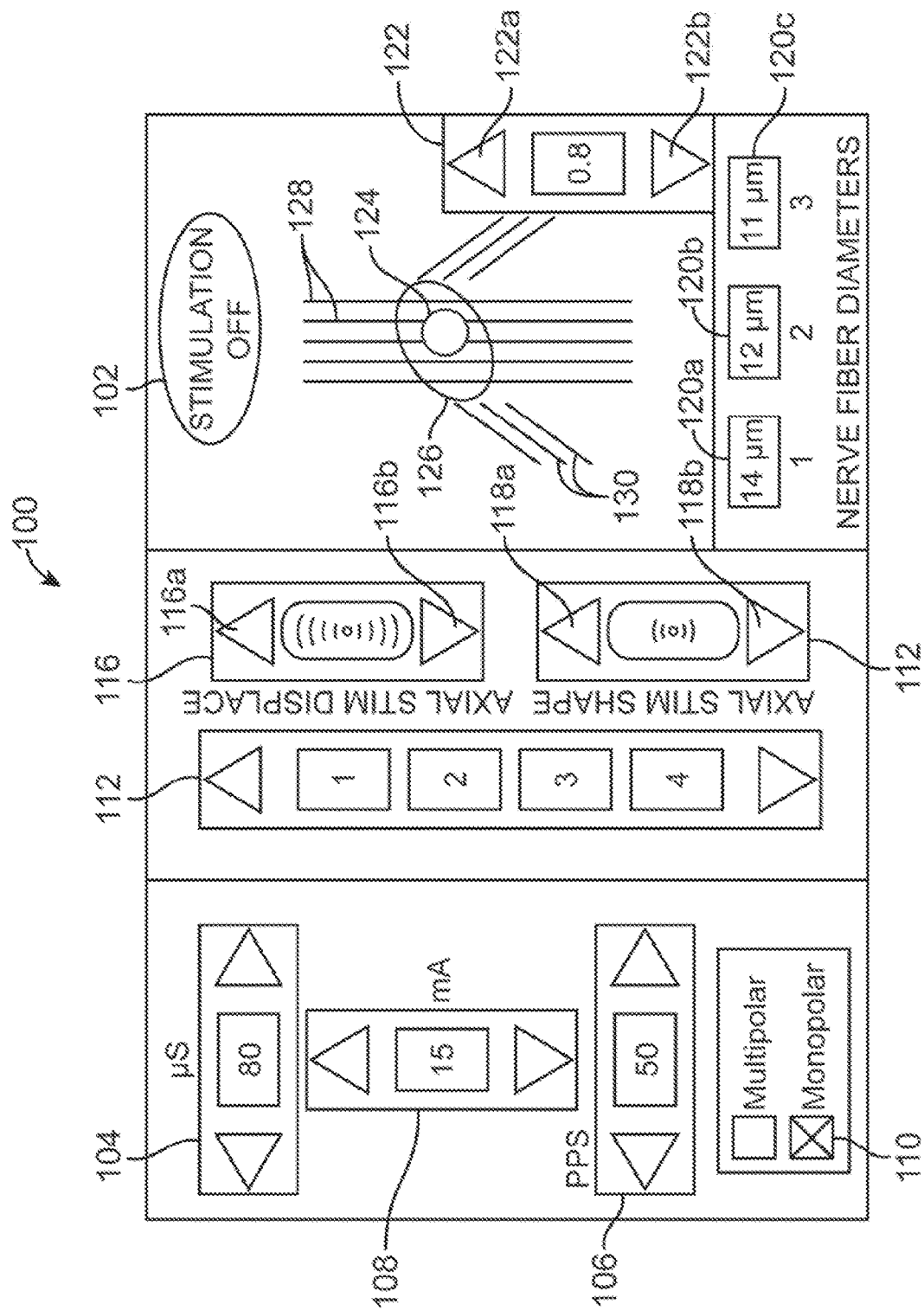
FIG. 7 is a plan view of a user interface of the CP of FIG. 6 for programming the IPG of FIG. 3.

In particular, a programming screen 100 can be generated by the CP 16, as shown in FIG. 7. The programming screen 100 allows a user to perform stimulation parameter testing. To this end, the programming screen 100 comprises a stimulation on/off control 102 that can be alternately clicked to turn the stimulation on or off. The programming screen 100 further includes various stimulation parameter controls that can be operated by the user to manually select stimulation parameter sets. In particular, the programming screen 100 includes a pulse width adjustment control 104 (expressed in microseconds (μs)), a pulse rate adjustment control 106 (expressed in pulses per second (pps)), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 44 of the IPG 14 may be treated as one of the lead electrodes 26, such that both the case electrode 44 and at least one of the lead electrodes 26 can be used to convey anodic electrical current at the same time. Additionally, the case electrode may be configured with all the programmability of a lead electrode, with full anodic and cathodic fractionalization.

The programming screen 100 also includes an electrode combination control 112 having arrows that can be clicked by the user to select one of four different electrode combinations 1-4. Each of the electrode combinations 1-4 can be created using a variety of control elements.

The programming screen 100 also includes a set of axial electrical stimulation field displacement control elements 116 and a set of axial electrical stimulation field shaping control elements 118. In the illustrated embodiments, the control elements 116, 118, as well as the other control elements discussed herein, are implemented as a graphical icon that can be clicked with a mouse or touched with a finger in the case of a touchscreen. Alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements.

When any of the axial electrical stimulation field displacement control elements 116 is actuated, control signals are generated in response to which the processor 80 is configured for generating stimulation parameter sets designed to axially displace the locus of the electrical stimulation field relative to the axis of the lead 12. Preferably, the control signals that are generated in response to the actuation of the control elements 116 or the alternative control elements are directional, meaning that the locus of the electrical stimulation field will be displaced in a defined direction in response to a continual actuation of a single control element irrespective of the current position of the locus electrical stimulation field locus. When any of the axial electrical stimulation field shaping control elements 118 is actuated, control signals are generated in response to which the processor 80 is configured for generating stimulation parameter sets designed to axially expand or contract the electrical stimulation field relative to its locus.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the processor 80 is configured for generating the plurality of stimulation parameter sets. The output telemetry circuitry 86 is configured for transmitting these stimulation parameters sets to the IPG 14.

Each of the sets of control elements 116, 118 takes the form of a double arrow (i.e., two oppositely pointing control element arrows) that can be actuated to modify the electrical stimulation field depending on the mode of operation. For example, an upper arrow control element 116a can be clicked to axially displace the locus of the electrical stimulation field (i.e., along the axis of the lead 12) in the proximal direction; a lower arrow control element 116b can be clicked to axially displace the locus of the electrical stimulation field (i.e., along the axis of the lead 12) in the distal direction; a lower arrow control element 118a can be clicked to axially contract the electrical stimulation field about its locus, and an upper arrow control element 118b can be clicked to axially expand the electrical stimulation field about its locus.

The locus of the electrical stimulation field may be displaced, e.g., by gradually "steering" or shifting electrical current between electrodes in a single timing channel. For example, the locus of the electrical stimulation field can be gradually displaced axially in the distal direction along the lead 12 by gradually including electrodes in a stimulating electrode group and gradually excluding other electrodes from the stimulating electrode group in the single timing channel.

The locus of the electrical stimulation field may alternatively be displaced using multiple timing channels. In particular, the electrical energy can be conveyed between different combinations of electrodes in accordance with multiple timing channels; that is, a first stimulating electrode group can be used during a first timing channel, a second stimulating electrode group can be used during a second timing channel, and so forth, and the groups may or may not overlap. The magnitude of the electrical energy conveyed in accordance with at least one of the multiple timing channels can be modified to effectively displace the locus of the stimulation region as experienced by the patient.

In the illustrated embodiment, the locus of the electrical stimulation field is represented by an ideal target pole (e.g., a cathode of an ideal bipole or ideal tripole) that can be arbitrarily steered around the electrode array 26 as fractionalized electrode combinations are computed to match the ideal target pole. Further details discussing the ideal target poles to arbitrarily steer electrical current within an electrode array are disclosed in U.S. patent application Ser. No. 12/938,282, entitled "System and Method for Mapping Arbitrary Electric Fields to Pre-Existing Lead Electrodes," which is expressly incorporated herein by reference.

The electrical stimulation field can be expanded and contracted by gradually "steering" or shifting electrical current between electrodes in a similar manner described above with respect to the displacement of the locus of the electrical stimulation field, with the exception that the electrical stimulation field is expanded or contracted.

For example, the electrical stimulation field can be gradually expanded axially along the lead 12 by gradually including electrodes in a stimulating electrode group, and can be gradually contracted axially along the lead 12 by gradually excluding electrodes in a stimulating electrode group. The electrical stimulation field can be alternatively expanded and contracted using multiple timing channels in a similar manner described above with respect to the displacement of the locus of the electrical stimulation field, with the exception that the electrical stimulation field is expanded or contracted. For example, the magnitude of the electrical energy conveyed in accordance with at least one of the multiple timing channels can be modified to effectively expand or contract the stimulation field.

Further details discussing different techniques for modifying an electrical stimulation field is disclosed in U.S. Provisional Patent Application 61/374,879, entitled "User Interface for Segmented Neurostimulation Leads," which is expressly incorporated herein by reference. In an optional embodiment, additional control elements can be provided to circumferentially displace the locus of the electrical stimulation field, circumferentially contract or expand the electrical stimulation field, radially displace the locus of the electrical field, or radially contract or expand the electrical stimulation field, as disclosed in U.S. Provisional Patent Application 61/374,879.

Although the programming screen 100 is described as allowing the electrical current to only be steered in one dimension, it should be appreciated that the programming screen 100 may allow the electrical current to be steering in two dimensions if the electrodes are arranged in two dimensions. In this case, using appropriate control elements (e.g., left and right arrows), the locus of the electrical stimulation field can be displaced in the transverse direction (perpendicular to the axial direction, and in this case, left or right) and/or the electrical stimulation field can be expanded or contracted in the transverse direction. Of course, the electrodes can be arranged in three-dimensions (e.g., by arranging three neurostimulation leads in three-dimensions or by using electrodes on a single neurostimulation lead that are arranged in three-dimensions, e.g., the segmented neurostimulation leads described in U.S. Provisional Patent Application Ser. No. 61/374,879), in which case, the electrical current can be steering in three-dimensions.

Although the ideal target pole discussed above provides an estimation of nerve activation points, the actual region of tissue activation will depend on the stimulation parameters, including the electrode spacings, pulse amplitude, and pulse width, as well as the configuration of the electrode array. Thus, the CP 18 will estimate a region or regions of tissue activation based on the stimulation parameter set or sets selected by the user via manipulation of the control elements.

Significantly, the accuracy of the region of tissue activation estimation will depend on how closely the diameter of the nerve fibers assumed for the estimation matches the actual diameter or diameters of the nerve fibers of the tissue adjacent the implanted electrodes. To this end, the programming screen 100 includes a means for the user to enter a diameter or diameters of nerve fibers. In the illustrated embodiment, the programming screen 100 includes control elements in the form of entry boxes 120, and in this case, three entry boxes 120a-120c, that allow the user to enter diameters of the nerve fibers in a conventional manner. These entered nerve fiber diameters will be assumed by the CP 18 when estimating regions of tissue activation for the currently selected stimulation parameter set. For example, as shown in FIG. 7, the user may enter nerve fiber diameters of 14 μm, 12 μm, and 11 μm, respectively for the nerve fibers. In alternative embodiments, other types of entry elements can be used to enter nerve fiber diameter information, such as pull-down menus or up/down arrows. Although it can be appreciated that the user-definition of the different nerve fiber diameters is quite useful in optimizing the estimation of the regions of activation, in an alternative embodiment, the different nerve fiber diameters may be fixed, such that they cannot be varied by the user.

Once entered, the processor 80 of the CP 18 will estimate regions of tissue activation for the entered nerve fiber diameters. In the illustrated embodiment, the processor 80 of the CP 18 will analytically determine (e.g., using a total net driving function, activating function, etc.) which nodes in a grid of uniformly spaced nodes (which may represent Nodes of Ranvier) would be activated by the electrical energy delivered in accordance with stimulation parameter set, e.g., in the manner described in U.S. Provisional Patent Application Ser. No. 61/427,059, entitled "Neurostimulation System for Implementing Model-Based Estimate of Neurostimulation Effects," which is expressly incorporated herein by reference. The regions of tissue activation can then be implied from the activated nodes. That is, for each nerve fiber diameter, a region of tissue activation bounding the activated nodes can be assumed.

Notably, modeling parameters other than nerve fiber diameter may be optionally selected by the user via the programming screen 100, thereby making the modeling of the neuronal response more flexible and allowing improvement in accuracy. For example, other modeling parameters that can be selected or otherwise defined by the user include neuronal membrane resistance, neuronal membrane capacitance and axoplasmic resistance, etc., or selection between an active model and a passive model, just to name a few.

Notably, the finer the resolution of the node grid, the more accurate the estimation of the regions of tissue activation, and the coarser the resolution of the node grid, the quicker that the regions of tissue activation can be estimated. Thus, there is a certain node grid resolution that provides a balance between accuracy and processing efficiency for the estimated regions of tissue activation, thereby allowing for an accurate real-time estimation of the regions of tissue activation as the stimulation parameter sets are varied by the user. The programming screen 100 includes a set of control elements 122 that allows the user to select the resolution of the node grid used by the processor 80 to estimate the regions of tissue activation. For example, an upper arrow control element 122a can be clicked to incrementally increase the grid resolution, and a lower arrow control element 122b can be clicked to incrementally decrease the grid resolution. In the illustrated embodiment, the node grid resolution may be varied in the range of 0.2 mm-2.0 mm. As will be described in further detail below, in addition to determining the regions of tissue activation, the processor 80 will also determine the relative probability that dorsal column (DC) nerve fibers traversing the estimated regions of tissue activation will be activated, and further, the dorsal root (DR) nerve fibers adjacent the estimated regions of tissue activation that will be activated. As a general rule, stimulation of the DC nerve fibers creates a therapeutic effect, and is therefore desirable, whereas stimulation of the DR nerve fibers create side-effects, and is therefore undesirable.

The programming screen 100 displays the ideal target pole 124 relative to the estimated regions of tissue activation 126, as well as the activated DC nerve fibers 128 and activated DR nerve fibers 130 adjacent the estimated regions of activation 126, thereby providing valuable feedback so that the user may efficiently program the IPG 14 that accurately targets the pain regions of the patient to be treated. The programming screen 100 may display the estimated regions of activation 126 over a grid of lines (with each intersection of two lines representing a node) in a variety of novel manners, using color as indicia for distinguishing the regions of activation respectively associated with the different nerve fiber diameters.

Figure 8A:
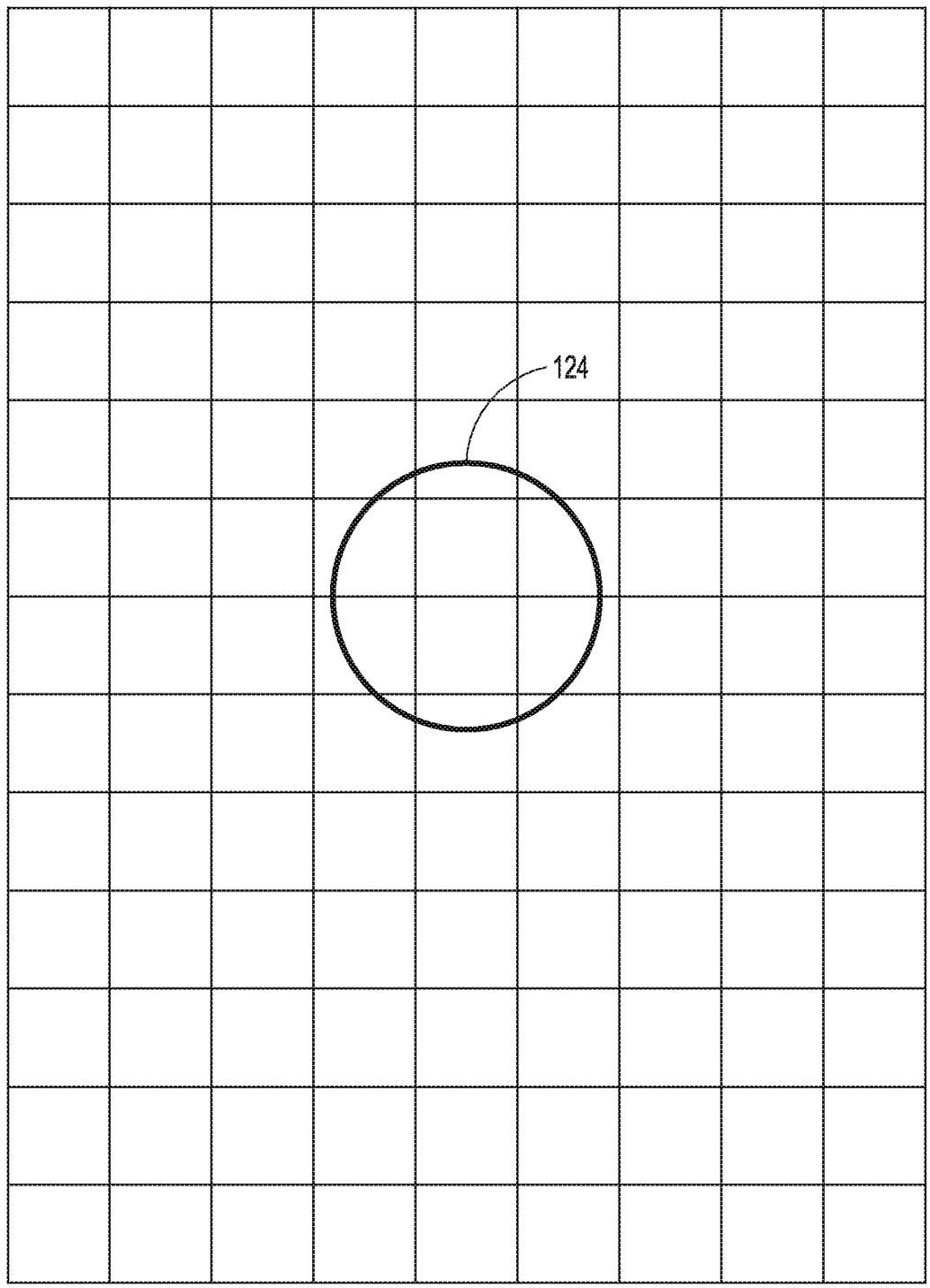
FIGS. 8a-8i are plan views of different manners of displaying regions of activation in the user interface of FIG. 7 that have been estimated for a single stimulation parameter set.
Figure 8B:
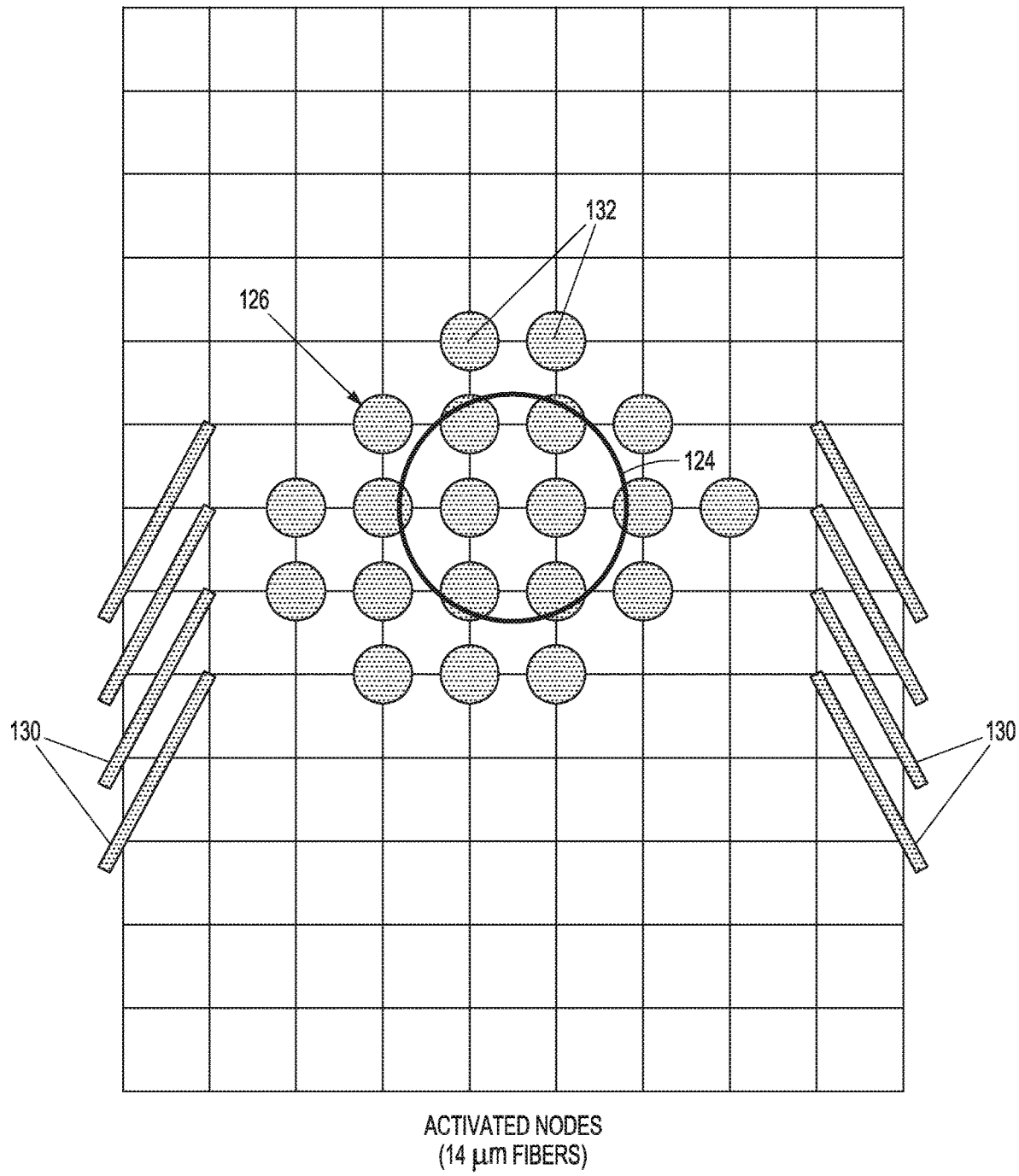

For example, as shown in FIG. 8*a*, if the amplitude of the electrical energy conveyed by the electrode array 26 is so low that no neural fibers are activated, only the ideal target pole 124 (represented by a grey circle) will be displayed over the steering space. As shown in FIG. 8*b*, when the amplitude of electrical energy is increased, the processor 80 will determine that certain nodes adjacent the ideal target pole will be activated. A representation of the activated nodes 132 will then be displayed. In the illustrated embodiment, the representation of the activated nodes 132 comprises discrete geometric shapes that are coincident with the activated nodes 132. In the illustrated embodiment, the geometric shapes are circles, which are all colored red, indicating that only one nerve fiber diameter (in this case, 14 µm) is assumed when estimating the region of tissue activation. A representation of the activated DR nerve fibers 130 is also displayed as red slashed parallel lines adjacent each transverse side of the estimated region of activation 126. Thus, with knowledge that DR nerve fibers 130 are activated, the user may modify the stimulation parameter set, such as by decreasing the amplitude of the electrical energy until no DR nerve fibers are displayed.

Figure 8C:
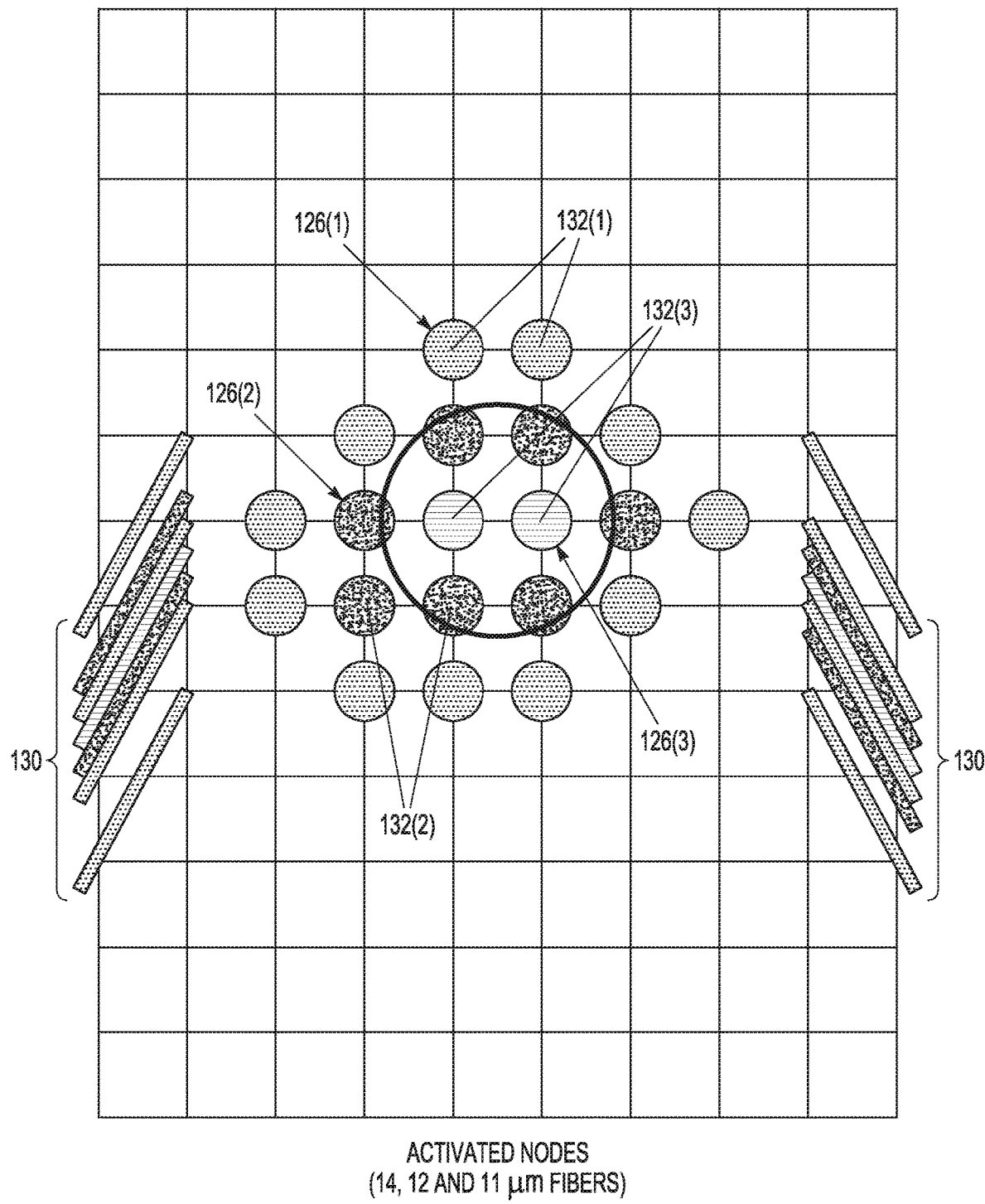

As shown in FIG. 8*c*, the circles representing the activated nodes 132 have different colors (in this case, three colors), indicating that multiple nerve fiber diameters are assumed when estimating regions of tissue activation. In this case, the blue circles represent nodes 132(1) that are activated when assuming a 11 µm diameter nerve fiber, thereby forming an estimated region of activation 126(1); the green circles represent nodes 132(2) that are activated when assuming a 12 µm diameter nerve fiber, thereby forming an estimated region of activation 126(2); and the red circles represent nodes 132(3) that are activated when assuming a 14 µm diameter nerve fiber, thereby forming an estimated region of activation 126(3). A representation of the activated DR nerve fibers 130 is also displayed as blue, green, and red slashed lines adjacent each transverse side of the estimated region of activation 126, indicating the DR nerve fibers 120 with the respective diameters (11 µm, 12 µm, and 14 µm) are activated.

It should be appreciated that, since smaller diameter nerve fibers are naturally less excitable than larger diameter nerve fibers, the estimated region of tissue activation will be relatively small for smaller diameter nerve fibers compared to the estimated region of tissue activation for the larger diameter nerve fibers. Thus, in the case illustrated in FIG. 8*c*, the estimated region of activation 126(2) formed by the green circles (12 µm diameter nerve fiber) will be larger than and surround the estimated region of activation 126(1) formed by the blue circles (11 µm diameter nerve fiber), and the estimated region of activation 126(3) formed by the red circles (14 µm diameter nerve fiber) will be larger than and surround both the estimated region of activation 126(2) formed by the green circles (12 µm diameter nerve fiber) and the estimated region of activation 126(1) formed by the blue circles (11 µm diameter nerve fiber).

The activated nodes and activated nerve fibers may be displayed in any one of a variety of manners, which may be user-defined. For example, in contrast to the embodiment illustrated in FIG. 8*b*, wherein all of the activated nodes 132 are represented as circles, the embodiment illustrated in FIG. 8*d* displays only the outline of the activated nodes 132(1) as circles; that is, only the activated nodes 132(1) bounding the estimated region of activation 126(1) is displayed, with the activated nodes in the center of the estimated region of activation 126(1) not being displayed. The red color in the circles indicates that the assumed nerve fiber diameter is 14 µm. Furthermore, in contrast to the embodiment illustrated in FIG. 8*b*, wherein the activated DR nerve fibers 130 are represented by slashed red lines, the embodiment illustrated in FIG. 8*d* displays the activated DR nerve fibers 130 as a solid colored geometric shape (in this case, a parallelogram) that encompasses all of the activated DR nerve fibers 130 on each side of the estimated region of activation 126(1). The red color in the circles representing the activated nodes 132(1) and the red color in the parallelograms representing the activated DR nerve fibers 130 indicates that the assumed nerve fiber diameter is 14 µm.

Figure 8D:
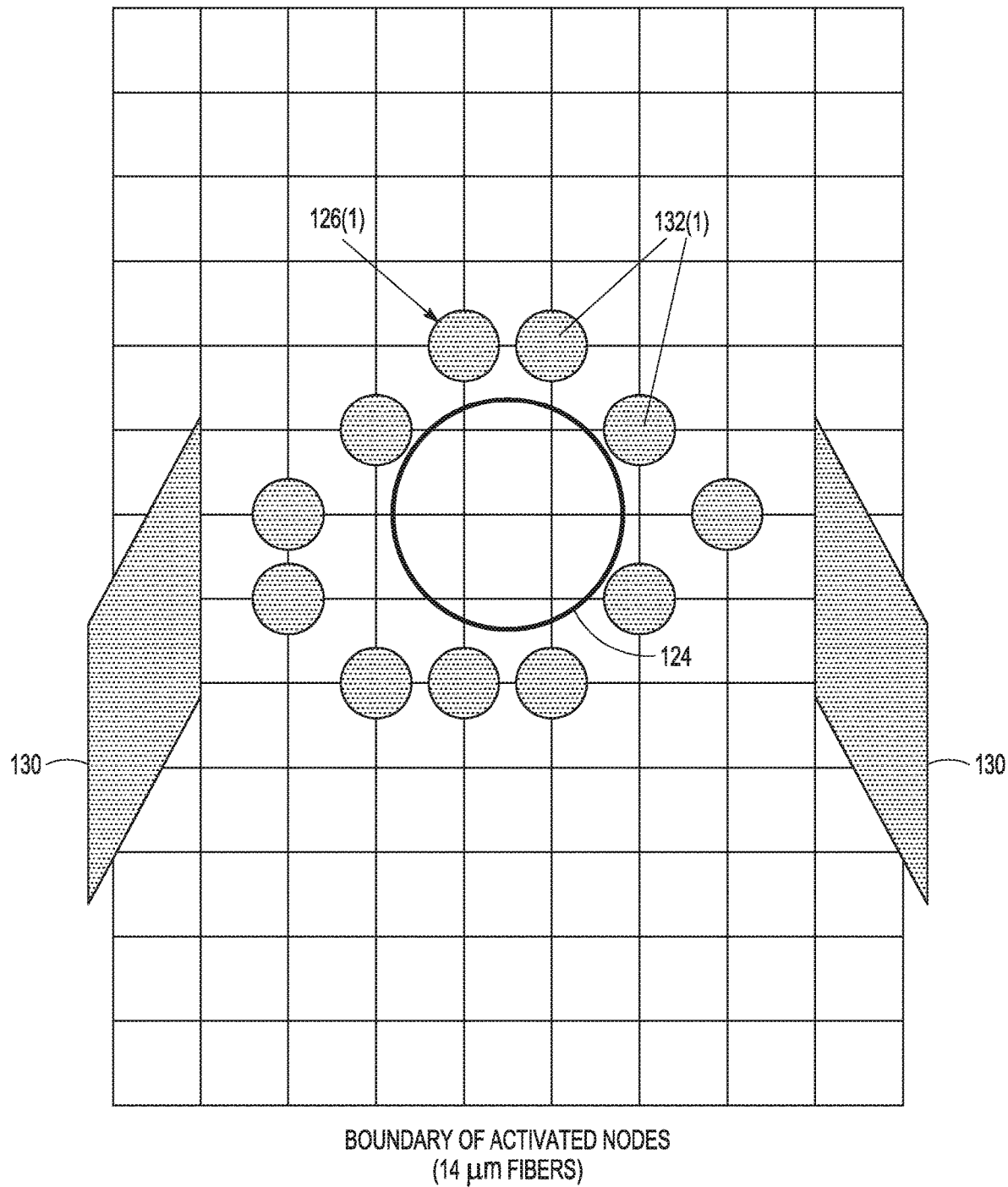
Figure 8E:
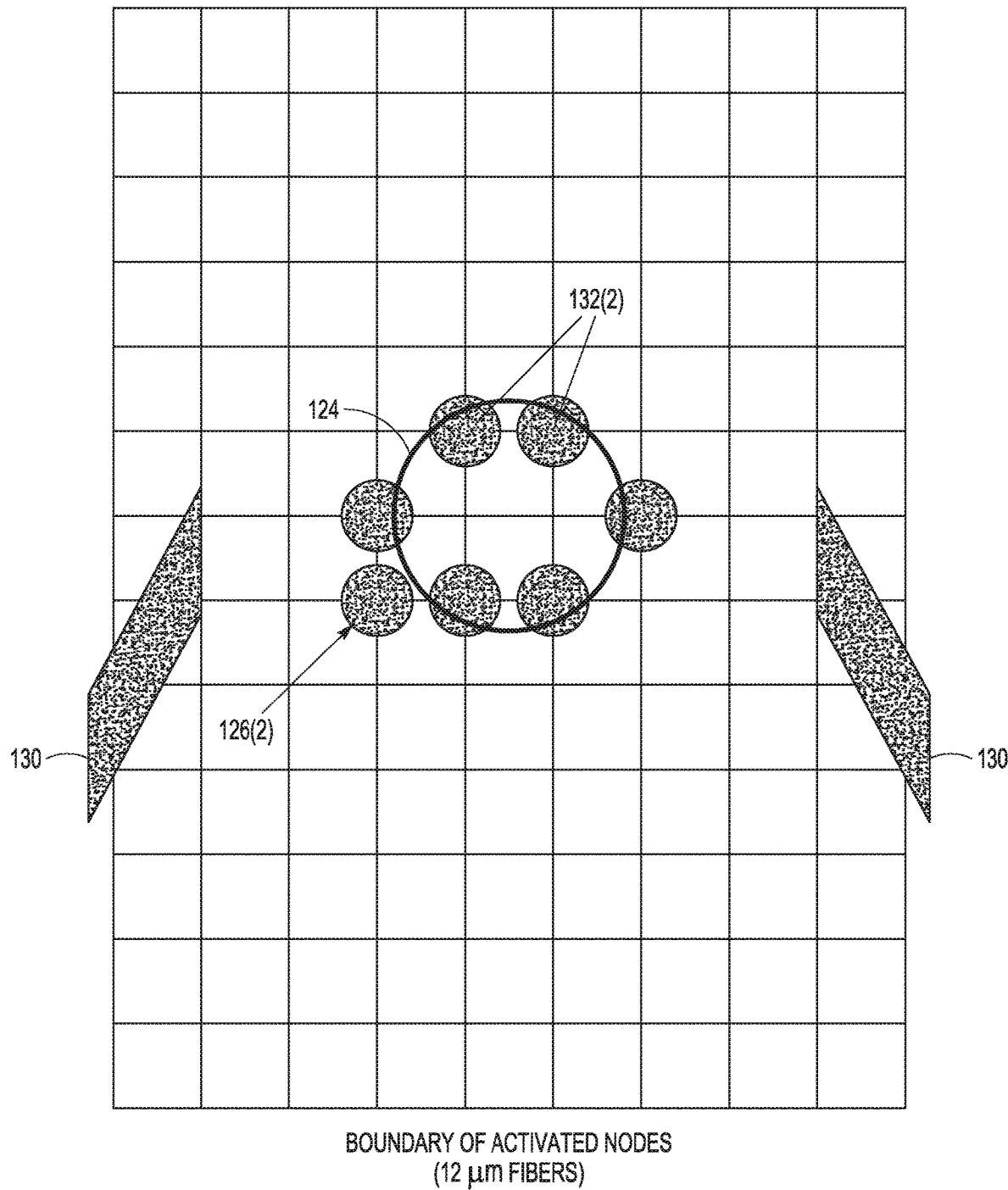

The embodiment illustrated in FIG. 8*e* is similar to the embodiment illustrated in FIG. 8*d*, with the exception that it assumes a nerve fiber diameter of 12 µm, in which case, the activated nodes 132(2) and DR nerve fibers 130 are respectively represented by green circles and green parallelograms. As can be appreciated, because the nerve fiber diameter assumed in the embodiment of FIG. 8*e* is smaller than the nerve fiber diameter assumed in the embodiment of FIG. 8*d*, the size of the estimated region of activation 126(2) and the representation of the activated DR nerve fibers 130 illustrated in FIG. 8*e* are smaller than the size of the estimated region of activation 126(1) and representation of the activated DR nerve fibers 130 illustrated in FIG. 8*d*.

Figure 8F:
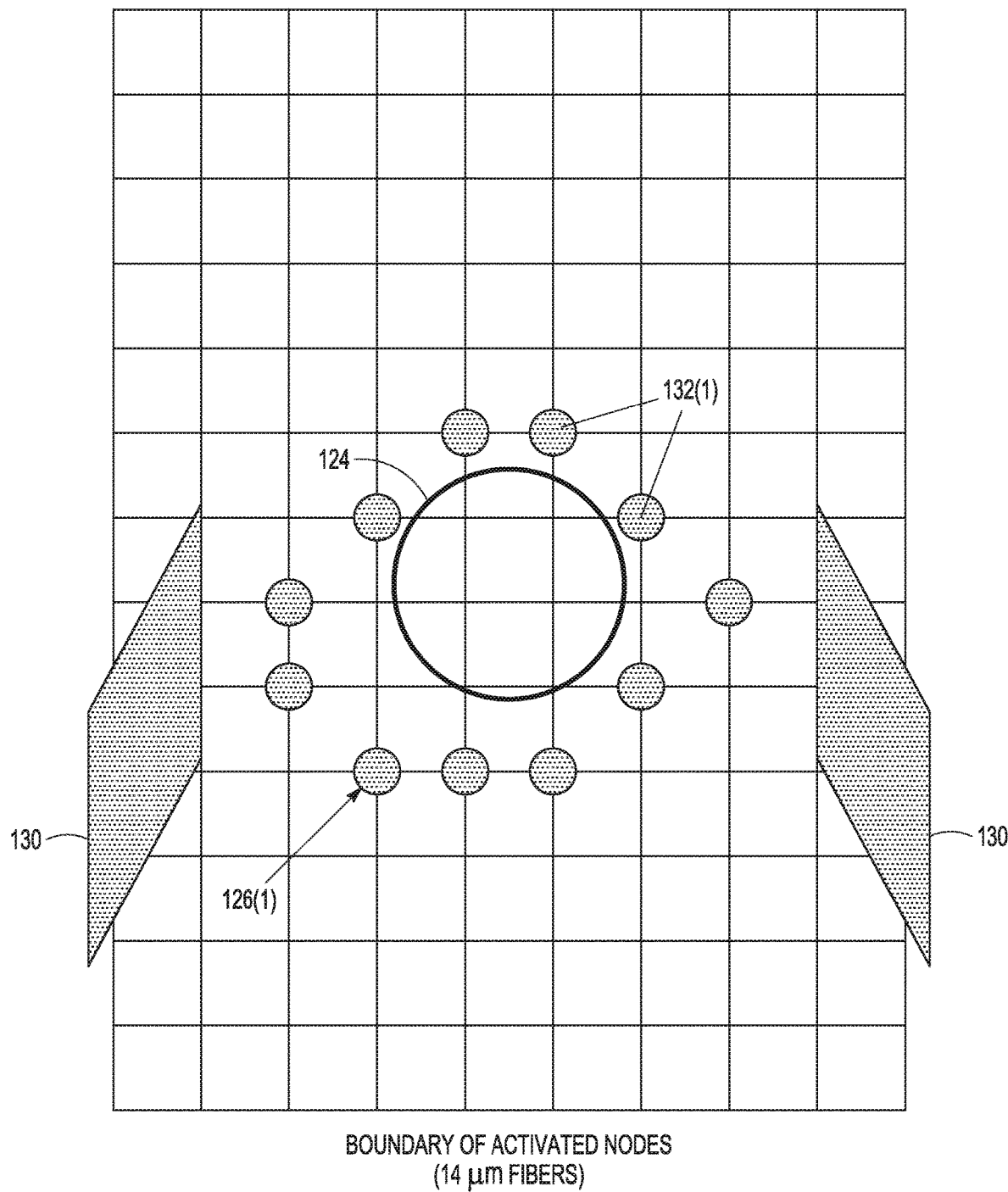
Figure 8G:
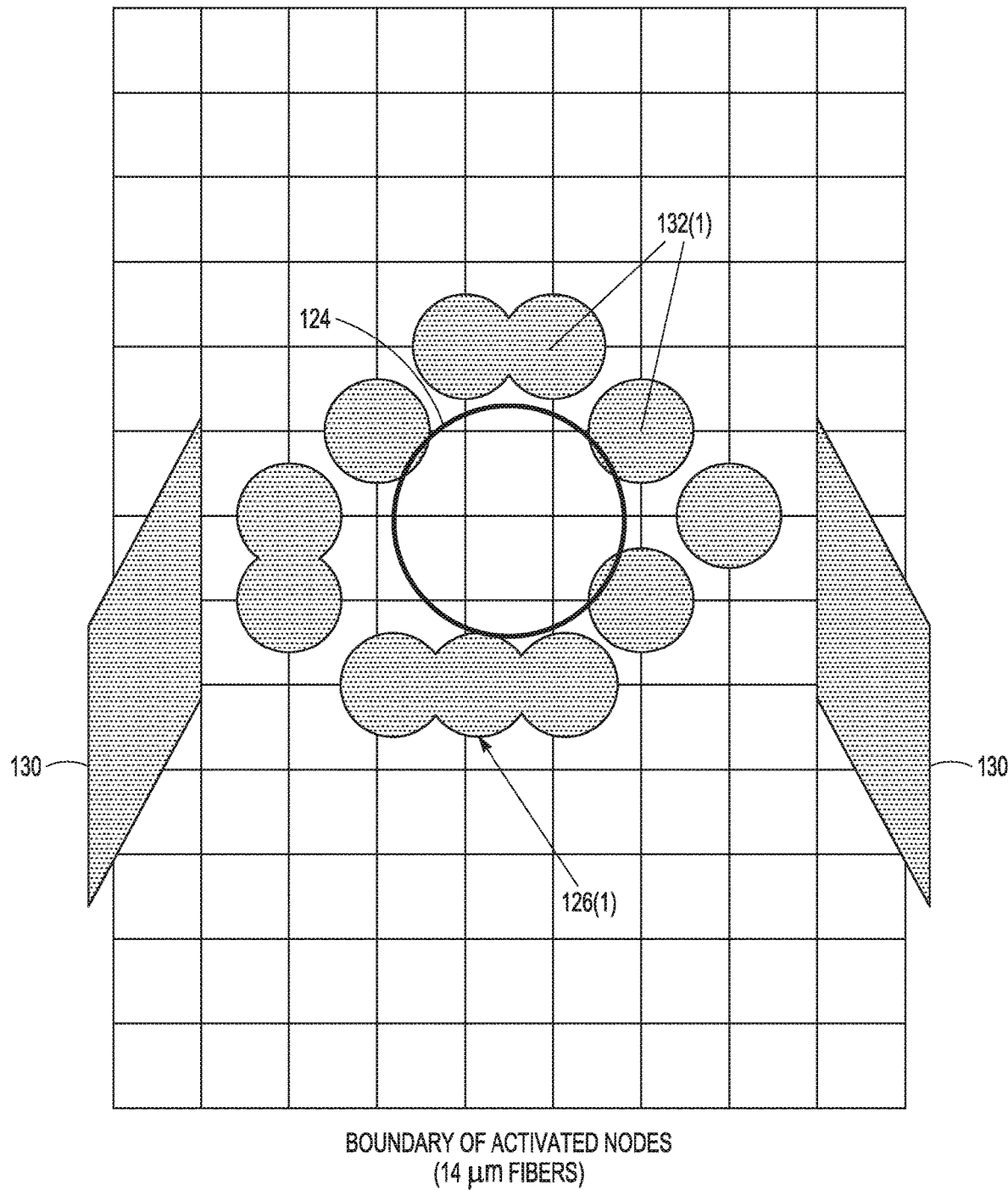
Figure 8H:
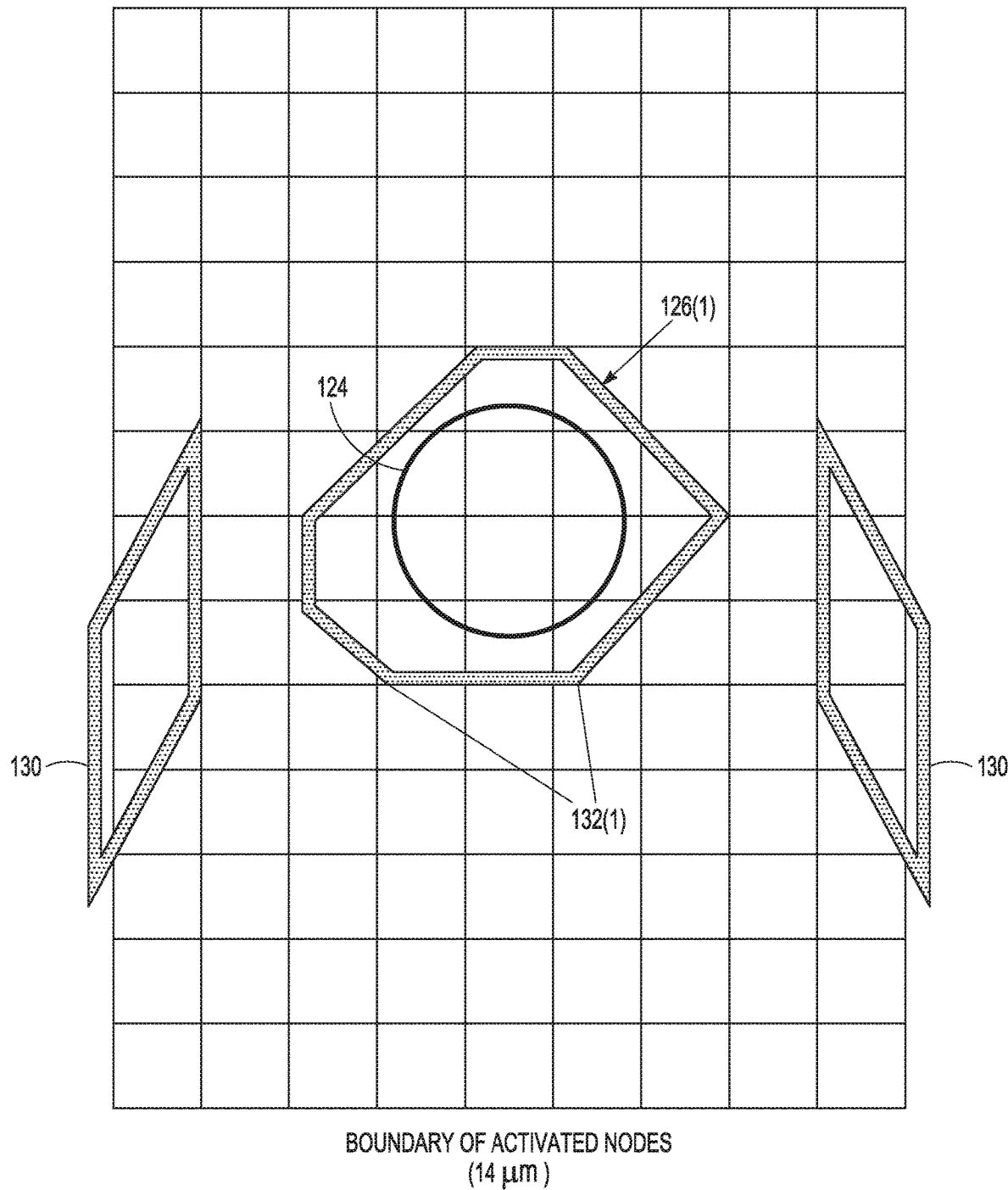

Although the size of the circles representing the activated nodes 132(1) in FIGS. 8*b*-8*e* have a specific size, the size of the circles may differ. For example, the embodiment illustrated in FIG. 8*f* is similar to the embodiment illustrated in FIG. 8*d*, with the exception that the size of the circles is smaller. As another example, the embodiment illustrated in FIG. 8*g* is similar to the embodiment illustrated in FIG. 8*d*, with the exception that the size of the circles is larger. Although the activated nodes 132(1) have been represented as discrete geometric shapes, such as circles, the activated nodes can be represented by the vertices of a polygon bounding the estimated region of activation, as shown in FIG. 8*h*. Furthermore, the parallelograms representing the activated DR nerve fibers 130 are not solid in the embodiment illustrated in FIG. 8*h*. Rather, only the outlines of the parallelograms are displayed.

Figure 8I:
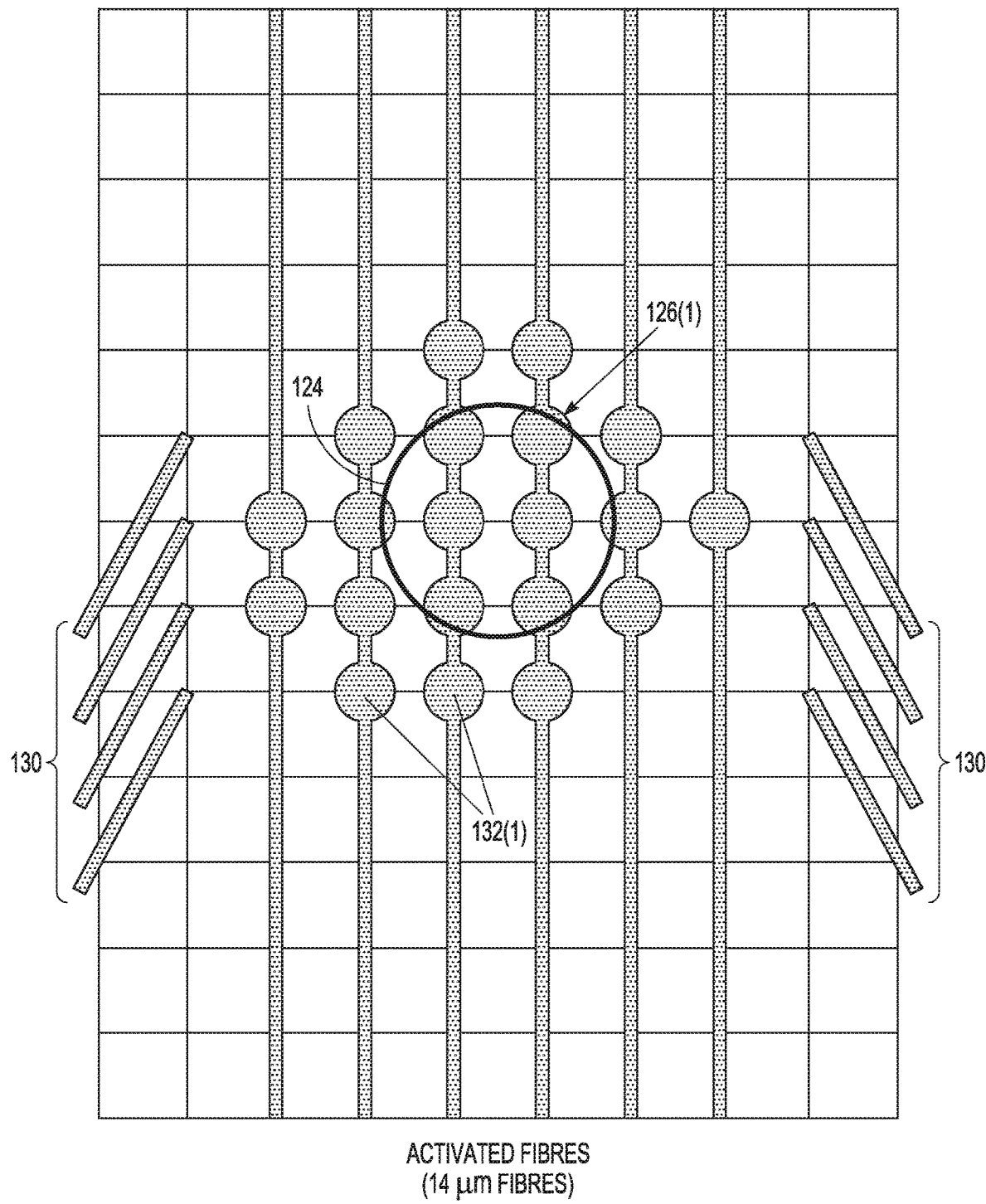

In an optional embodiment illustrated in FIG. 8*i*, the processor 80 is configured for determining the intensity of activation within the estimated region of activation at points transversely spaced relative to the DC nerve fibers 128, which are represented by parallel lines intersecting the points. In the illustrated embodiments, the points are coincident with the activated nodes 132. Preferably, the highest intensity activated node that intersects each DC nerve fiber 128 is used as the highest intensity value. The parallel lines 128 have indicia of the activation intensities that have been determined at the corresponding points. For example, the thicknesses of the lines 128 may be proportional to the intensities determined at the corresponding points (i.e., the thicker the lines, the higher the intensity of the activation). The lines 128 are colored red, indicating that a nerve diameter of 14 µm is assumed for the DC nerve fibers 128.

Referring to FIGS. 9 and 10, an optional embodiment of the programming screen 100 allows the user to associate different estimated regions of tissue activation with regions of paresthesia that the patient feels. In contrast to the embodiment of FIG. 8c, wherein multiple regions of activation are estimated for a single stimulation parameter set, the regions of activation illustrated in FIG. 9 have been estimated respectively from different stimulation parameter sets.

Figure 9A:
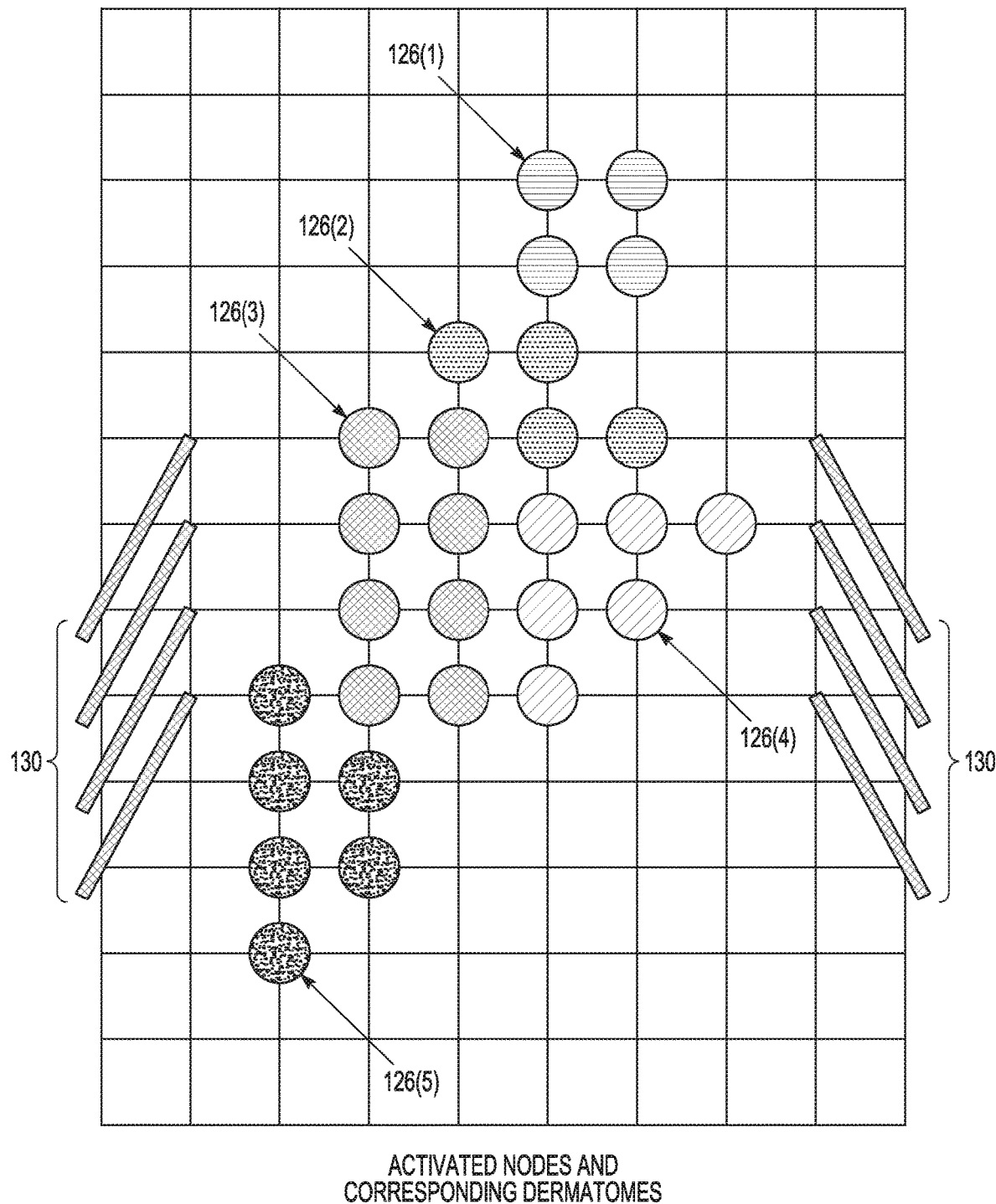
FIGS. 9a-9b are plan views of different manners of display regions of activation in the user interface of FIG. 7 that have been estimated for multiple stimulation parameter sets.
Figure 9B:
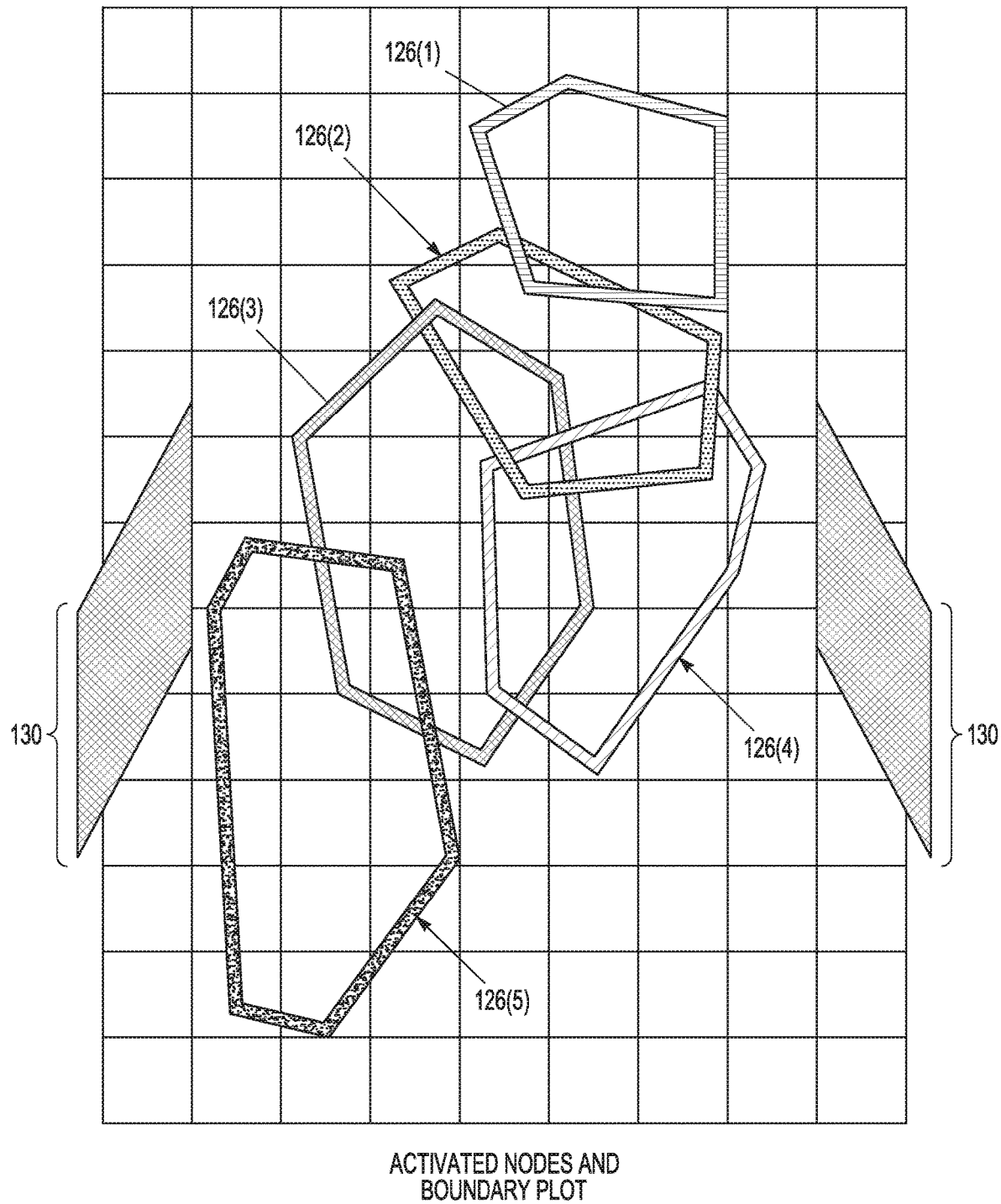

In particular, the programming screen 100 allows the user to select different stimulation parameter sets, and for each selected stimulation parameter set, the processor 80 of the CP 18 estimates a region of activation 126, which is displayed to the user in the manner discussed above. In this case, however, only one nerve fiber diameter is assumed when estimating the regions of activation, and the regions of activation 126 are distributed about the neural tissue in order to provide therapy to the different regions of the patient. As shown in FIG. 9a, the activated nodes 132 from which the different regions of activation 126 can be implied are represented by circles coincident with the activated nodes 132, and activated DR nerve fibers 130 are represented by slashed parallel lines. As shown in FIG. 9b, the activated nodes 132 from which the different regions of activation 126 can be implied are represented by polygon vertices coincident with the activated nodes 132, and activated DR nerve fibers 130 are represented by solid parallelograms on each side of the regions of activation 126.

Figure 10B:
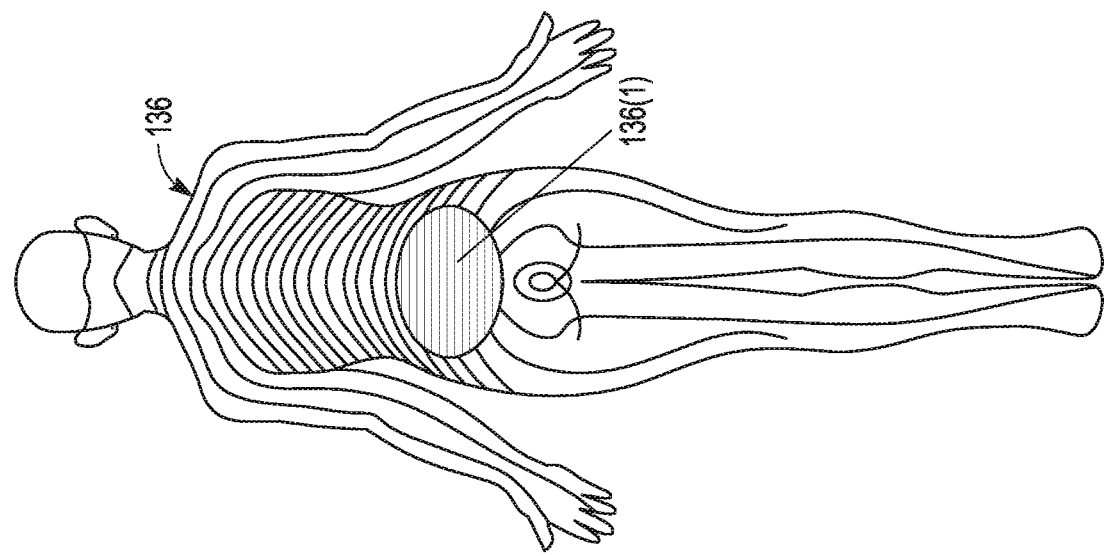
FIGS. 10a-10b are anterior and posterior views of a human pain map, wherein different regions of the human pain map have been color-coded with the corresponding estimated regions of activation displayed in FIGS. 9a-9b.
Figure 10A:
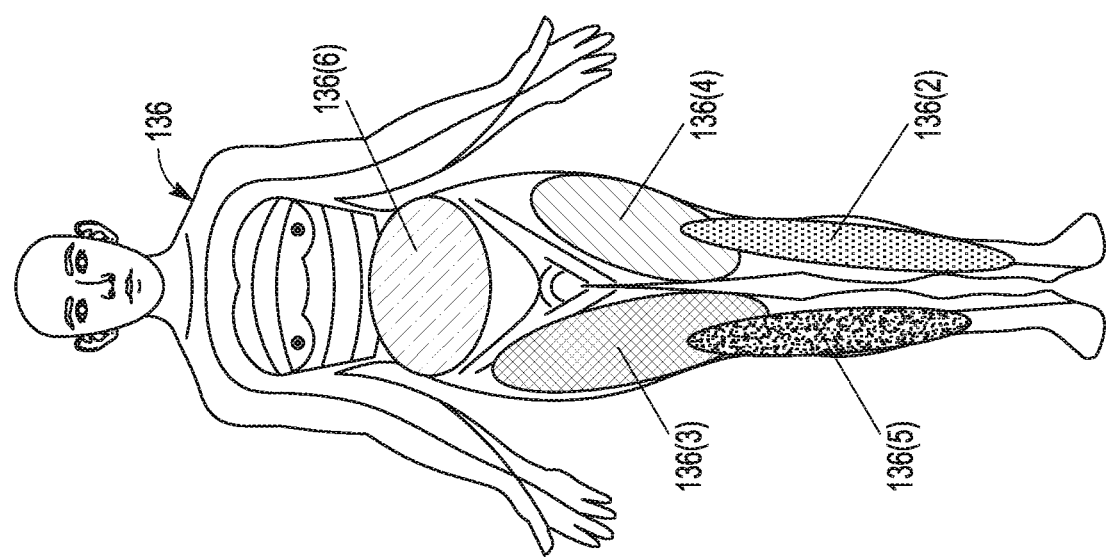

The programming screen 100 also allows the user to select a plurality of different tissue regions for therapy via a human body map 136 illustrated in FIG. 10a (anterior human body map) and FIG. 10b (posterior human body map). Any region of the human map 136 can be clicked to select that region for therapy. Alternatively, the regions may be selected simply by free drawing on the human body map. In the illustrated embodiment, the lower back 136(1), lower left leg 136(2), right thigh 136(3), left thigh 136(4), right lower leg 136(5), and abdomen 136(6) have been highlighted for therapy.

Indicia in the form of colors are used to associate the displayed regions for therapy to the displayed estimated regions of tissue activation 126 and activated DR nerve fibers 130. For example, the color blue is used to associate the lower back 136(1) to the estimated region of tissue activation 126(1); the color red is used to associate the lower left leg 136(2) to the estimated region of tissue activation 126(2); the color purple is used to associate the right thigh 136(3) to the estimated region of tissue activation 126(3); the color yellow is used to associate the left thigh 136(4) to the estimated region of tissue activation 126(4); the color green is used to associate the right lower leg 136(5) to the estimated region of tissue activation 126(5); and the color pink is used to associate the abdomen 136(6) to the estimated activated DR nerve fibers 130.

Presumably, each pain region 136 is a dermatome corresponding to the spinal cord tissue covered by the respective region of tissue activation 126. During selection of each stimulation parameter set, feedback from the patient can be used to ensure that the electrical energy delivered in accordance with the stimulation parameter set optimally provides the necessary paresthesia for the corresponding pain region 136. Once optimal paresthesia is achieved for the stimulation parameter set, the region of tissue activation 126 or activated DR nerve fibers 130 estimated for this stimulation parameter set, which are matched to the corresponding pain regions 136 using color, can be recorded. Based on this technique, superficial tissue on the spinal cord will generate a dermatome map specific to the patient, with color-matched dermatomes providing visual identification of paresthesia coverage linked to a specific stimulation parameter set. Once this dermatome map is generated, a user may subsequently steer an ideal target pole immediately over any of the neural locations coincident with the recorded estimated regions of activation 126 or activated DC nerve fibers 130.

Although the foregoing techniques have been described as being implemented in the CP 18, it should be noted that this technique may be alternatively or additionally implemented in the RC 16, and the processing functions of the technique can even be performed in the IPG 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system comprising:
a neural stimulator configured to stimulate target neural tissue without a side effect caused by stimulating other neural tissue;
a user input device configured to allow a user to select a set of stimulation parameters for the neural stimulator to stimulate the target neural tissue;
a display;
processing circuitry connected to the user input device and the display, wherein the processing circuitry is configured to:
provide together on the display representations including a first representation indicative of an electrical stimulation field based on the user-selected set of stimulation parameters for the neural stimulator, a second representation indicative of the target neural tissue, and a third representation indicative of the other neural tissue;
change the display in response to estimating that the user-selected set of stimulation parameters will stimulate the target neural tissue to indicate when the user-selected set of stimulation parameters is estimated to stimulate the target neural tissue; and
change the display in response to estimating that the user-selected set of stimulation parameters will stimulate the other neural tissue to indicate when the user-selected set of stimulation parameters is estimated to stimulate the other neural tissue and cause the side effect; and
output circuitry configured to transmit the user-selected set of stimulation parameters to the neural stimulator for use by the neural stimulator to stimulate the target neural tissue.

2. The system of claim 1, wherein the second representation is displayed as a first color and the third representation is displayed as a second color.

3. The system of claim 1, wherein the user input device is configured to allow the user to select the target neural tissue to be stimulated by the neural stimulator using the set of stimulation parameters.

4. The system of claim 3, wherein the processing circuitry is configured to represent different target neural tissue on the display with different colors.

5. The system of claim 4, wherein the different target neural tissue includes different nerve fiber diameters.

6. The system of claim 1, wherein processing circuitry is configured to change the display in response to estimating that the user-selected set of stimulation parameters will stimulate the target neural tissue by changing from not displaying the second representation to displaying the second representation when it is estimated that the user-selected set of stimulation parameters will stimulate the target neural tissue.

7. The system of claim 1, wherein processing circuitry is configured to change the display in response to estimating that the user-selected set of stimulation parameters will stimulate the other neural tissue by changing from not displaying the third representation to displaying the third representation when it is estimated that the user-selected set of stimulation parameters will stimulate the target neural tissue.

8. The system of claim 1, wherein the selected stimulation parameter set comprises an electrode combination, wherein the user input device is further configured to enable a user to define a target pole relative to the one or more electrodes, wherein the target pole indicates a locus of the electrical stimulation field and the third representation indicates the target pole, and wherein the processing circuitry is further configured to determine the electrode combination based on the defined target pole.

9. The system of claim 1, wherein the target neural tissue includes spinal cord tissue.

10. A method for using a system comprising a neural stimulator, user input device, processing circuitry and a display, the method comprising:
using the user input device to receive a user selection of a set of stimulation parameters for the neural stimulator to stimulate the target neural tissue;
using the processing circuitry to provide together on the display representations including a first representation indicative of an electrical stimulation field based on the user-selected set of stimulation parameters for the neural stimulator, a second representation indicative of the target neural tissue, and a third representation indicative of the other neural tissue;
using the processing circuitry to change the display in response to estimating that the user-selected set of stimulation parameters will stimulate the target neural tissue to indicate when the user-selected set of stimulation parameters is estimated to stimulate the target neural tissue;
using the processing circuitry to change the display in response to estimating that the user-selected set of stimulation parameters will stimulate the other neural tissue to indicate when the user-selected set of stimulation parameters is estimated to stimulate the other neural tissue and cause the side effect;
transmitting the user-selected set of stimulation parameters to the neural stimulator for use by the neural stimulator to stimulate the target neural tissue; and
stimulating the target neural tissue using the neural stimulator, wherein the neural stimulator uses the transmitted user-selected set of stimulation parameters to stimulate the target neural tissue.

11. The method of claim 10, wherein using the processing circuitry to change the display in response to estimating that the user-selected set of stimulation parameters will stimulate the target neural tissue includes changing from not displaying the second representation to displaying the second representation when it is estimated that the user-selected set of stimulation parameters will stimulate the target neural tissue.

12. The method of claim 11, wherein using the processing circuitry to change the display in response to estimating that the user-selected set of stimulation parameters will stimulate the other neural tissue includes changing from not displaying the third representation to displaying the third representation when it is estimated that the user-selected set of stimulation parameters will stimulate the target neural tissue.

13. The method of claim 11, wherein the second representation is displayed as a first color and the third representation is displayed as a second color.

14. The method of claim 11, further comprising using the user input device to allow the user to select the target neural tissue to be stimulated by the neural stimulator using the set of stimulation parameters.

15. The method of claim 14, further comprising using the processing circuitry to represent different target neural tissue on the display with different colors.

16. A non-transitory computer-readable storage media including instructions, which when executed by a system that comprises a neural stimulator, a user input device, processing circuitry and a display, cause the system to perform a method comprising:
using the user input device to receive a user selection of a set of stimulation parameters for the neural stimulator to stimulate the target neural tissue;
using the processing circuitry to provide together on the display representations including a first representation indicative of an electrical stimulation field based on the user-selected set of stimulation parameters for the neural stimulator, a second representation indicative of the target neural tissue, and a third representation indicative of the other neural tissue;
using the processing circuitry to change the display in response to estimating that the user-selected set of stimulation parameters will stimulate the target neural tissue to indicate when the user-selected set of stimulation parameters is estimated to stimulate the target neural tissue;
using the processing circuitry to change the display in response to estimating that the user-selected set of stimulation parameters will stimulate the other neural tissue to indicate when the user-selected set of stimulation parameters is estimated to stimulate the other neural tissue and cause the side effect;
transmitting the user-selected set of stimulation parameters to the neural stimulator for use by the neural stimulator to stimulate the target neural tissue; and
stimulating the target neural tissue using the neural stimulator, wherein the neural stimulator uses the transmitted user-selected set of stimulation parameters to stimulate the target neural tissue.

17. The non-transitory computer-readable storage media of claim 16, wherein using the processing circuitry to change the display in response to estimating that the user-selected set of stimulation parameters will stimulate the target neural tissue includes changing from not displaying the second representation to displaying the second representation when it is estimated that the user-selected set of stimulation parameters will stimulate the target neural tissue.

18. The non-transitory computer-readable storage media of claim 16, wherein using the processing circuitry to change the display in response to estimating that the user-selected set of stimulation parameters will stimulate the other neural tissue includes changing from not displaying the third representation to displaying the third representation when it is estimated that the user-selected set of stimulation parameters will stimulate the target neural tissue.

19. The non-transitory computer-readable storage media of claim 16, wherein the second representation is displayed as a first color and the third representation is displayed as a second color.

20. The non-transitory computer-readable storage media of claim 16, wherein the method performed by the system further comprises using the user input device to allow the user to select the target neural tissue to be stimulated by the neural stimulator using the set of stimulation parameters, and using the processing circuitry to represent different target neural tissue on the display with different colors.

* * * * *